(12) United States Patent
Uludag et al.

(10) Patent No.: US 11,964,057 B2
(45) Date of Patent: Apr. 23, 2024

(54) TRANSFECTION REAGENTS FOR DELIVERY OF NUCLEIC ACIDS

(71) Applicant: RJH BIOSCIENCES INC., Edmonton (CA)

(72) Inventors: Hasan Uludag, Edmonton (CA); Remant Badahur Kc, Edmonton (CA); Juliana Valencia-Serna, Edmonton (CA)

(73) Assignee: RJH BIOSCIENCES INC. (CA)

( * ) Notice: Subject to any disclaimer, the term of this patent is extended or adjusted under 35 U.S.C. 154(b) by 739 days.

(21) Appl. No.: 16/621,502

(22) PCT Filed: Jun. 18, 2018

(86) PCT No.: PCT/CA2018/050737
§ 371 (c)(1),
(2) Date: Dec. 11, 2019

(87) PCT Pub. No.: WO2018/232502
PCT Pub. Date: Dec. 27, 2018

(65) Prior Publication Data
US 2021/0154149 A1 May 27, 2021

Related U.S. Application Data

(60) Provisional application No. 62/522,448, filed on Jun. 20, 2017.

(51) Int. Cl.
*A61K 47/18* (2017.01)
*A61K 9/51* (2006.01)
(Continued)

(52) U.S. Cl.
CPC .......... *A61K 9/5146* (2013.01); *A61K 9/5192* (2013.01); *A61K 47/18* (2013.01);
(Continued)

(58) Field of Classification Search
CPC ...................................................... A61K 47/18
See application file for complete search history.

(56) References Cited

U.S. PATENT DOCUMENTS 6,696,038 B1   2/2004 Mahato
7,183,263 B2   2/2007 Furgeson et al.
(Continued)

OTHER PUBLICATIONS

Abbasi M, Lavasanifar A, Berthiaume LG, Weinfeld M, Uludag H. Cationic polymer-mediated small interfering RNA delivery for P-glycoprotein down-regulation in tumor cells. Cancer. 2010; 116:5544-54.

(Continued)

*Primary Examiner* — Benjamin J Packard
(74) *Attorney, Agent, or Firm* — Kirsten M. Oates; Rodman & Rodman LLP

(57) ABSTRACT

Polymeric transfection reagents for delivery of nucleic acids to cells, pharmaceutical compositions comprising same, and methods of preparing and using same are provided. A compound comprises polyethylenimine, a lipid selected from cholesterol, lauric acid, palmitic acid, or stearic acid, and optionally, a histidine. A nanoparticle comprises the compound complexed to a nucleic acid. A composition or pharmaceutical composition comprises the nanoparticle and a pharmaceutically acceptable carrier, anti-fouling agent, targeting ligand, or combinations thereof. A method of treating, preventing, or ameliorating a disease in a subject comprises administering to the subject an effective amount of the nanoparticle or the composition or pharmaceutical composition.

30 Claims, 20 Drawing Sheets
Specification includes a Sequence Listing.

(51) Int. Cl.
    A61K 47/54    (2017.01)
    A61K 47/59    (2017.01)
    C07J 41/00    (2006.01)
    C12N 15/88    (2006.01)
(52) U.S. Cl.
    CPC ............ *A61K 47/554* (2017.08); *A61K 47/59* (2017.08); *C07J 41/0055* (2013.01); *C12N 15/88* (2013.01)

(56) References Cited

U.S. PATENT DOCUMENTS

2004/0142474 A1    7/2004    Mahato
2006/0127482 A1*   6/2006    Fewell ................... A61K 31/17
                                                        514/45

OTHER PUBLICATIONS

Aigner A, Fischer D, Merdan T, Brus C, Kissel T, Czubayko F. Delivery of unmodified bioactive ribozymes by an RNA-stabilizing polyethylenimine (LMW-PEI) efficiently down-regulates gene expression. Gene therapy. 2002;9:1700-7.

Aliabadi HM, Mahdipoor P, Uludag H. Polymeric delivery of siRNA for dual silencing of Mcl-1 and P-glycoprotein and apoptosis induction in drug-resistant breast cancer cells. Cancer gene therapy. 2013;20:169-77.

Assmann G, Nofer Jr. Atheroprotective effects of high-density lipoproteins. Annual review of medicine. 2003;54:321-41.

Baccarani M, Cortes J, Pane F, Niederwieser D, Saglio G, Apperley J, et al. Chronic myeloid leukemia: an update of concepts and management recommendations of European LeukemiaNet. Journal of clinical oncology : official journal of the American Society of Clinical Oncology. 2009;27:6041-51.

Bahadur KC, Landry B, Aliabadi HM, Lavasanifar A, Uludag H. Lipid substitution on low molecular weight (0.6-2.0 kDa) polyethylenimine leads to a higher zeta potential of plasmid DNA and enhances transgene expression. Acta biomaterialia. 2011;7:2209-17.

Bajaj A, Kondaiah P, Bhattacharya S. Synthesis and gene transfection efficacies of PEI-cholesterol-based lipopolymers. Bioconjugate chemistry. 2008;19:1640-51.

Bolcato-Bellemin AL, Bonnet ME, Creusat G, Erbacher P, Behr JP. Sticky overhangs enhance siRNA-mediated gene silencing. Proceedings of the National Academy of Sciences of the United States of America. 2007;104:16050-5.

Chabaud P, Camplo M, Payet D, Serin G, Moreau L, Barthelemy P, et al. Cationic nucleoside lipids for gene delivery. Bioconjugate chemistry. 2006;17:466-72.

Duxbury MS, Ashley SW, Whang EE. RNA interference: a mammalian SID-1 homologue enhances siRNA uptake and gene silencing efficacy in human cells. Biochemical and biophysical research communications. 2005;331:459-63.

Godbey WT, Wu KK, Mikos AG. Tracking the intracellular path of poly(ethylenimine)/DNA complexes for gene delivery. Proceedings of the National Academy of Sciences of the United States of America. 1999;96:5177-81.

Godbey WT, Wu KK, Mikos AG. Size matters: molecular weight affects the efficiency of poly(ethylenimine) as a gene delivery vehicle. Journal of biomedical materials research. 1999;45:268-75.

Goldman JM, Melo JV. Chronic myeloid leukemia—advances in biology and new approaches to treatment. The New England journal of medicine. 2003;349:1451-64.

Grzelczak M, Vermant J, Furst EM, Liz-Marzan LM. Directed self-assembly of nanoparticles. ACS nano. 2010;4:3591-605.

Hsu CY, Uludag H. Cellular uptake pathways of lipid-modified cationic polymers in gene delivery to primary cells. Biomaterials. 2012;33:7834-48.

Kim WJ, Chang CW, Lee M, Kim SW. Efficient siRNA delivery using water soluble lipopolymer for anti-angiogenic gene therapy. Journal of controlled release : official journal of the Controlled Release Society. 2007; 118:357-63.

Landry B, Aliabadi HM, Samuel A, Gul-Uludag H, Jiang X, Kutsch O, et al. Effective non-viral delivery of siRNA to acute myeloid leukemia cells with lipid-substituted polyethylenimines. PloS one. 2012;7:e44197.

Landry B, Valencia-Serna J, Gul-Uludag H, Jiang X, Janowska-Wieczorek A, Brandwein J, et al. Progress in RNAi-mediated Molecular Therapy of Acute and Chronic Myeloid Leukemia. Molecular therapy Nucleic acids. 2015;4:e240.

Larsen HO, Roug AS, Nielsen K, Sondergaard CS, Hokland P. Nonviral transfection of leukemic primary cells and cells lines by siRNA—a direct comparison between Nucleofection and Accell delivery. Experimental hematology. 2011;39:1081-9.

Ley TJ et al. (Cancer Genome Atlas Research Network). Genomic and epigenomic landscapes of adult de novo acute myeloid leukemia. N Engl J Med. 2013;368:2059-74.

Linder ME, Deschenes RJ. New insights into the mechanisms of protein palmitoylation. Biochemistry. 2003;42:4311-20.

Lungwitz U, Breunig M, Blunk T, Gopferich A. Polyethylenimine-based non-viral gene delivery systems. European Journal of pharmaceutics and biopharmaceutics : official journal of Arbeitsgemeinschaft fur Pharmazeutische Verfahrenstechnik eV. 2005;60:247-66.

Mahato RI, Lee M, Han S, Maheshwari A, Kim SW. Intratumoral delivery of p2CMVmIL-12 using water-soluble lipopolymers. Molecular therapy : the Journal of the American Society of Gene Therapy. 2001;4:130-8.

Marra E, Palombo F, Ciliberto G, Aurisicchio L. Kinesin spindle protein SiRNA slows tumor progression. Journal of cellular physiology. 2013;228:58-64.

McNamara JO, 2nd, Andrechek ER, Wang Y, Viles KD, Rempel RE, Gilboa E, et al. Cell type-specific delivery of siRNAs with aptamer-siRNA chimeras. Nature biotechnology. 2006;24:1005-15.

Mintzer MA, Simanek EE. Nonviral vectors for gene delivery. Chemical reviews. 2009;109:259-302.

Remant Bahadur KC CKaHU. Additive nanocomplexes of cationic lipopolymers for improved non-viral gene delivery to mesenchymal stem cells. J Mater Chem B. 2015;3:10.

Ren R. Mechanisms of BCR-ABL in the pathogenesis of chronic myelogenous leukaemia. Nature reviews Cancer. 2005;5:172-83.

Sarli V, Giannis A. Targeting the kinesin spindle protein: basic principles and clinical implications. Clinical cancer research : an official journal of the American Association for Cancer Research. 2008;14:7583-7.

Schiffer CA. BCR-ABL tyrosine kinase inhibitors for chronic myelogenous leukemia. The New England journal of medicine. 2007;357:258-65.

Soutschek J, Akinc A, Bramlage B, Charisse K, Constien R, Donoghue M, et al. Therapeutic silencing of an endogenous gene by systemic administration of modified siRNAs. Nature. 2004;432:173-8.

Teo PY, Yang C, Hedrick JL, Engler AC, Coady DJ, Ghaem-Maghami S, et al. Hydrophobic modification of low molecular weight polyethylenimine for improved gene transfection. Biomaterials. 2013;34:7971-9.

Valencia-Serna J, Gul-Uludag H, Mahdipoor P, Jiang X, Uludag H. Investigating siRNA delivery to chronic myeloid leukemia K562 cells with lipophilic polymers for therapeutic BCR-ABL down-regulation. Journal of Controlled Release. 2013;172:495-503.

Wang DA, Narang AS, Kotb M, Gaber AO, Miller DD, Kim SW, et al. Novel branched poly(ethylenimine)-cholesterol water-soluble lipopolymers for gene delivery. Biomacromolecules. 2002;3:1197-207.

Zhou LL, Zhao Y, Ringrose A, DeGeer D, Kennah E, Lin AE, et al. AHI-1 interacts with BCR-ABL and modulates BCR-ABL transforming activity and imatinib response of CML stem/progenitor cells. J Exp Med. 2008;205:2657-71.

* cited by examiner

TRANSFECTION REAGENTS FOR DELIVERY OF NUCLEIC ACIDS

This application incorporates by reference the material in the ASCII text file named "SEQUENCE LISTING", in computer readable form (CRF). The Sequence Listing was created on Oct. 16, 2020. The size of the text file is 2 KB.

FIELD OF THE INVENTION

The present invention relates to polymeric transfection reagents for delivery of nucleic acids to cells, pharmaceutical compositions comprising same, and methods of preparing and using same.

BACKGROUND OF THE INVENTION

Polynucleotides are large, anionic macromolecules which cannot enter cells on their own and cannot exert any biological effect in the absence of a carrier. The delivery of polynucleotides may be accomplished by various physical or chemical methods. Physical methods may include for example, disruption of the cell membrane by a force (e.g., electric current or pressure) to create holes through which polynucleotides can penetrate the cell membrane. However, this is usually a toxic process and damage may be induced in the cells, leading to cell death or undesirable effects. Chemical methods may involve use of transfection reagents such as lipid-based carriers (e.g., liposomes, lipid particles, solid nucleic acid lipid particles, SNALP) and cationic molecules (e.g., oligomers or larger cationic macromolecules). Lipids are hydrophobic and require organic solvents for processing. Small polyamines (e.g., spermine and related compounds) have been modified with lipids for transfection. Poly(amino acids) such as poly(lysine) have also been modified with various reagents for the same end.

However, conventional carriers display toxic effects at concentrations suitable for delivery of polynucleotides to cells. Primary cells are difficult to transfect due to their sensitivity to carrier concentration, leading to significant cell death or undesirable changes in cellular physiology. Their uptake (endocytosis) mechanisms are also slower such that they do not readily display uptake of external reagents. In this regard, attachment-dependent cells, which constitute the majority of cells in human body, usually display relatively higher surface area and active endocytosis. However, attachment independent cells that grow in suspension such as blood cells or cells found in soft tissues intimate with interstitial fluids such as bone marrow, spleen and lymph nodes, are highly sensitive to the presence of carriers at low concentrations, have a low surface area and display low uptake rates.

The ability to transfect anchorage independent cells with polynucleotides is highly desirable for therapeutic applications. These cells are found circulating in the body and can be localized in the blood stream or other soft tissues in intimate contact with circulating blood such as bone marrow space, spleen, and lymph nodes. Often abnormal cells from other tissues, which are normally attachment-dependent, are also shed into circulation when they display metastatic features and become attachment-independent. Such cells survive in an attachment-independent manner in circulating blood and related fluids until recruited and attached to other sites. Diseases involving uncontrolled proliferation of these attachment-independent cells are especially common in the population and cause significant morbidity and mortality among patients.

Representative diseases that arise from uncontrolled proliferation of attachment independent cells include various leukemias, of which the most common are acute myeloid leukemia, chronic myeloid leukemia, acute lymphocytic leukemia, chronic lymphocytic leukemia, myelodysplastic disorders that produce inefficient hematopoiesis, myeloproliferative disorders that over-produce blood cells in bone marrow, polycythemias, thrombocythemias, multiple myeloma, and various lymphomas including Hodgkin and non-Hodgkin lymphomas. These diseases arise from molecular alterations in the genes that control the balance of growth, differentiation and apoptosis, and lead to clonal expansion of certain cell types at the expense of other cell types. Accumulation of genetic abnormalities may lead to malignancies that result in permanent alterations of cell population in circulation. The genetic abnormalities can manifest itself in different forms, from single (point) mutations changing the nature of a critical site in a particular gene (and resulting function), to gene fusions where large fragments of genetic segments are mobilized and juxta-positioned to create abnormally activated proteins.

Examples of abnormal genes involving single gene defects or fusion proteins can be found in various sources. For example, Landry et al. (2015) list single gene defects that are associated with various leukemias that could serve as therapeutic targets: KIF11, FLT3, STAT3, STAT5A/B, RRM2, FLT1, RUNX1, Cyclin A2, Hsp70, p65, p100/52 (NfkB), HIF-1a, GFI-1B, Hsp27, Hsp32, CXCR4, CD44, Nucleoplasmin, ID family of proteins, CD22, and MAX dimerization protein 3 (MDX3), to name some representative examples. Fusion genes that are of therapeutic value for myeloproliferative disorders are listed in Lay et al. (2015): BCR-ABL, ETV6-ABL, ZNF198-FGFR1, FOP-FGFR1, CEP110-FGFR1, BCR-FGFR1, ETV6-PDGFRB, HIP1-PDGFRB, H4-PDGFRB, RAB5-PDGFRB, ETV6-JAK2, BCR-JAK2, ETV6-SYK2, PML-RARA, MYH11-CBFB, RUNX1-RUNX1T1, PICALM-MLLT10/AF10, NUP98-NSD1, and multiple fusions involving MLL, to name some representative examples.

As a specific example, chronic myeloid leukemia (CML) is a hematopoietic stem cell disease characterized by acquired abnormalities in chromosomal chromosome 22 called Philadelphia chromosome (31). These chromosomes arise from reciprocal translocations of Abelson murine leukemia (c-Abl) gene located on 9q to breakpoint cluster region (BCR) on 22q. The resultant BCR-Abl chimeric protein exhibits constitutively activated tyrosine kinase activity, alters cell adhesion to bone marrow stroma, increases cell proliferation, and reduces apoptosis (14 33). CML therapies based on small molecular drugs, such as tyrosine-kinase inhibitors, and stem cell transplantation suffer from acquired drug resistance and risk of mortality from chronic graft-versus-host diseases (5 14).

To target BCR-Abl kinase specifically, short interfering RNA (siRNA) is ideal since siRNA molecules work at the molecular level to interact directly with abnormal mRNA targets that cause cellular overgrowth (19). Since BCR-Abl gene fusion in this disease creates a unique molecular entity, whose equivalent does not exist in normal cells, it can serve as a very specific target for siRNA therapies. However, effective delivery of siRNA remains problematic. The siRNAs are polynucleotides with rigid helical structure that hampers complexation with non-viral vectors, which limits the therapeutic efficacy of the resultant systems (8). Safe carriers based on synthetic materials are needed that capable of intracellular transport of siRNA without eliciting immune reaction or genomic integration (29). Synthetic materials function by electrostatically interacting with siRNA and creating nanoparticles suitable for cellular binding and uptake. The siRNA delivery to anchorage-independent CML cells has been particularly challenging. The lack of an exposed surface area and lack of proteoglycans on the cell surface limit the uptake of complexes from conventional cationic carriers (20). Hence most researchers have employed non-specific electroporation for delivering nucleic acids to leukemic cells in culture (19). In this approach, an electrical current is passed through the cell membrane to make transient holes to allow nanoparticle uptake, but this approach cannot be used for clinical therapy of the disease.

Polyethylenimine (PEI) has emerged as a multipurpose carrier due to its chemical versatility and high cationic charge suitable for polynucleotide interactions (2 11, 23). The efficacy of PEI is generally proportional to its molecular weight, but the non-biodegradable nature of high molecular weight PEI along with its high cellular toxicity is problematic when used on highly sensitive human cells (12 13). Low molecular weight PEIs are more biocompatible with human cells and could be cleared easier in the body due to their smaller size, but they are not effective in delivery of polynucleotides. These polymers are employed as starting materials to design effective reagents by chemical modification with different moieties such as hydrophobic molecules, hydrophilic molecules, targeting ligands etc. The modification with aliphatic lipids generally enhanced the efficacy of the parent polymers via increased membrane interaction and intracellular uptake (3, 6, 22, 30). These lipopolymers effectively undertook siRNA delivery to anchorage dependent cells (e.g., breast cancer cells), although the efficacy was dependent on the origin of the cells. A highly lipid-substituted PEI (1.2 kDa PEI having about 2 palmitic acids/PEI) was also an effective siRNA carrier in CIVIL cells as compared to polymers with lower lipid substitution (36).

Cholesterol (Chol) has been used in non-viral gene delivery either by direct conjugating onto siRNAs or by grafting onto cationic polymers and peptide (7, 10, 17, 24-26). U.S. Pat. No. 6,696,038 discloses a method for the synthesis of amide-conjugated cholesterol grafted PEI (MW 0.6 to 25000 kDa) for the delivery of bioactive agents such as DNA, RNA, oligonucleotides, proteins, peptides, and drugs into in vitro and in vivo models. Only high molecular weight PEIs (MW>1800 Da) generated water soluble derivatives, while low molecular weight PEIs (MW<1800 Da) were water insoluble. For in vivo application, these polymers required helper lipids (e.g. DOPE). In US Pat. Appin. Publ. No. 2004/0142474, cholesterol grafted PEIs with PEGylation were explored only for DNA delivery in a carcinoma tumor model derived from attachment-dependent cell lines. U.S. Pat. No. 7,183,263 disclosed cholesterol grafted linear PEI (MW 25000 kDa) for application in gene delivery to an attachment-dependent carcinoma model. Limited Chol integration onto carriers generates water-soluble lipophilic carriers, which display significant efficacy in non-viral gene delivery (34). The specific affinity of Chol toward lipoprotein particles further helps the polyplexes to navigate in physiological systems (4). Chol-grafted low molecular weight PEIs have been employed for DNA delivery as well as in liposomal formulations with helper lipids (7, 9), but not in leukemia therapy or other disorders caused by uncontrolled proliferation of anchorage-independent cells.

Accordingly, there is a need for safer, effective carriers which do not affect the cells adversely and can undertake efficient delivery of polynucleotides.

SUMMARY OF THE INVENTION

The present invention relates to polymeric transfection reagents for delivery of nucleic acids to cells, pharmaceutical compositions comprising same, and methods of preparing and using same.

In one aspect, the invention comprises a compound comprising a polymer and a lipid, the polymer having a molecular weight ranging from about 0.5 kDa to about 5.0 kDa. In one embodiment, the polymer is selected from polyethylenimine, polyalkylimine, a poly(amino acid), a poly(beta-amino acid), a poly(beta-amino ester), a cationic amino acid containing a peptide or a polymer, an aminated polymer derived from water-soluble, uncharged polymers modified with amine compounds, polyethylenimine derivatized with silica, polyethylenglycol, polypropyleneglycol, an amino acid, dopamine, poly(2-dimethylaminoethyl methacrylate or a derivative thereof in combination with a polymer to create amphiphilic polymers; a polyamidoamine derivative; and poly(N-(2-hydroxypropyl)methacrylamide) or a derivative thereof. In one embodiment, the lipid is selected from an aliphatic lipid where the length of carbon changes from C3 to C22, an unsaturated version of an aliphatic lipid, triglyceride, cholesterol or a derivative thereof, a phospholipid, a synthetic lipidic compound, a multicyclic lipid, or a steroid.

In one embodiment, the polymer comprises polyethylenimine in a branched or linear form, and the lipid is selected from cholesterol or a derivative thereof, lauric acid, palmitic acid, or stearic acid. In one embodiment, the derivative of cholesterol comprises cholic acid or deoxycholic acid. In one embodiment, polyethylenimine has a molecular weight selected from 0.6 kDa, 1.2 kDa, or 2.0 kDa, and the lipid comprises cholesterol. In one embodiment, the polymer comprises polyethylenimine in a branched or linear form, the lipid selected from cholesterol or a derivative thereof, and the amino acid histidine.

In one embodiment, the compound has the formula:

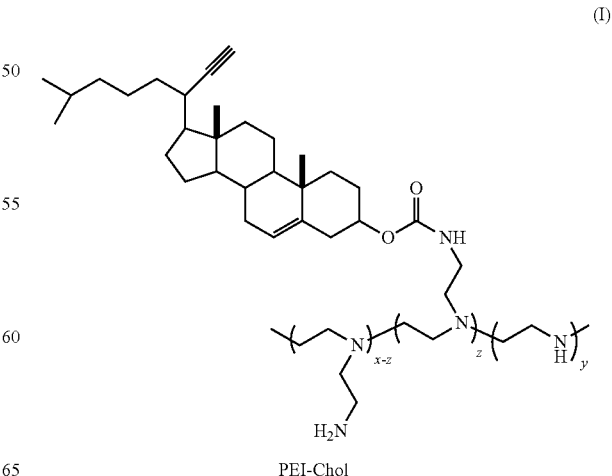

(I)

PEI-Chol

In one embodiment, the compound has the formula:

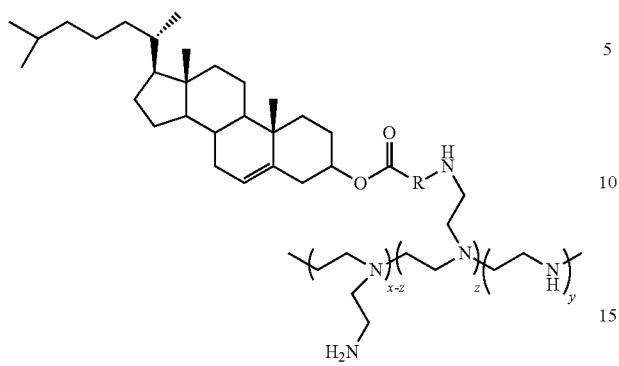

(II)

where a linker R comprises a spacer of $0<n<10$ atoms and a cleavable chemical group. In one embodiment, the cleavable chemical group in R is selected from a disulfide, thioester, ester, orthoester, anhydride, phosphoester, acetal, ketal, or carbonate.

In one embodiment, the compound has the formula:

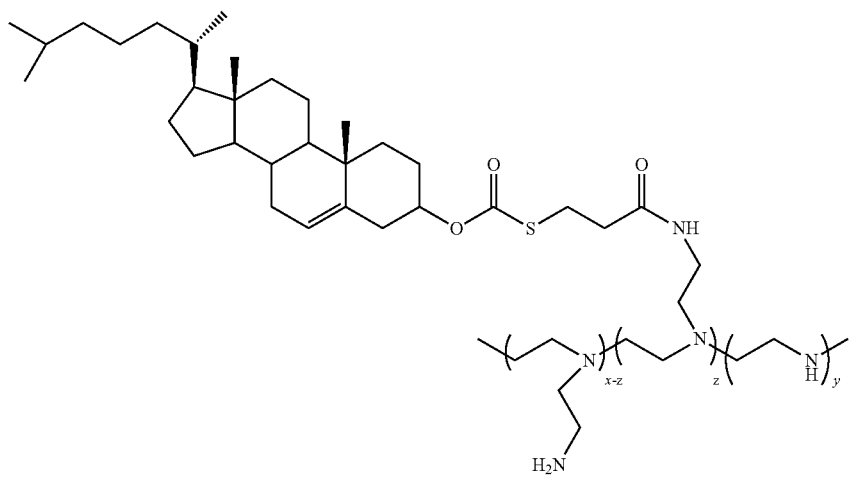

(IIa)

In one embodiment, the compound has the formula:

(IIb)

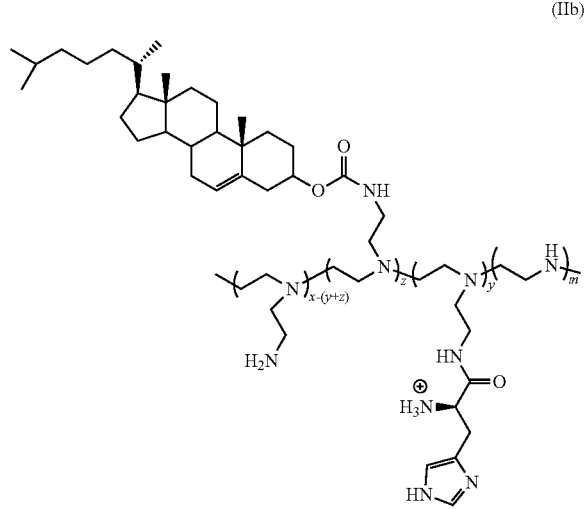

In one aspect, the invention comprises a nanoparticle comprising any of the above compounds complexed to a nucleic acid. In one embodiment, the nucleic acid comprises siRNA, microRNA, a DNA-based oligonucleotide or antisense oligonucleotide, a peptide-nucleic acid, DNA-RNA chimeras, plasmid DNA intended to code for short hairpin RNA, messenger RNA, or combinations thereof. In one embodiment, the nanoparticle comprises one or more siRNAs against a target gene.

In one aspect, the invention comprises a composition or pharmaceutical composition comprising the above nanoparticle, and a pharmaceutically acceptable carrier, a targeting ligand, an anti-fouling agent, or combination thereof. In one embodiment, the nanoparticle comprises polyethylenimine having a molecular weight selected from 0.6 kDa, 1.2 kDa, or 2.0 kDa, cholesterol, and siRNA.

In one aspect, the invention comprises a method of preparing the above composition or pharmaceutical composition comprising the steps of:
a) dissolving each of a polymer, a nucleic acid, and one or more of an anti-fouling agent and a targeting ligand in an aqueous-based buffer or a cell culture medium to yield a polymer solution, a nucleic acid solution, an anti-fouling agent solution, and a targeting ligand solution;

b) mixing the polymer solution and the nucleic acid solution at a ratio ranging from about 1 to about 10 (w/w) to yield a polymer-nucleic acid solution;

c) incubating the polymer-nucleic acid solution; and d) adding the anti-fouling agent solution or the targeting ligand solution followed by incubation to yield the composition or pharmaceutical composition.

In one aspect, the invention comprises a method of treating, preventing, or ameliorating a disease in a subject, comprising administering to the subject an effective amount of the above nanoparticle or the above composition or pharmaceutical composition. In one embodiment, the nanoparticle comprises polyethylenimine, cholesterol, and siRNA, or a composition or pharmaceutical composition comprising same. In one embodiment, the disease comprises chronic myeloid leukemia, acute myeloid leukemia, chronic lymphocytic leukemia, acute lymphocytic leukemia, hairy cell leukemia, meningeal leukemia, myeloma, multiple myeloma, lymphoma, non-Hodgkin lymphoma, Hodgkin lymphoma, Sezary Syndrome, and the like.

In another aspect, the invention comprises use of the above nanoparticle or the above composition or pharmaceutical composition to treat, prevent, or ameliorate a disease in a subject.

In yet another aspect, the invention comprises a kit comprising a polymeric transfection reagent; a nucleic acid; and one or more pharmaceutically acceptable carriers, targeting ligands, anti-fouling agents, or a combination thereof. In one embodiment, the kit further comprises one or more reagents, utensils and vessels for combining the polymeric transfection reagent; the nucleic acid; and the one or more pharmaceutically acceptable carriers, targeting ligands, anti-fouling agents, or a combination thereof an applicator for administering the pharmaceutical composition to the subject; and instructions for preparing and administering the pharmaceutical composition.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings.

and Stearic Acid (StA) were prepared and tested. The analysis is summarized as the relative cell viability compared to the cells without any treatment (taken as 100%), *p<0.01, **p<0.001.

Figure 11A:
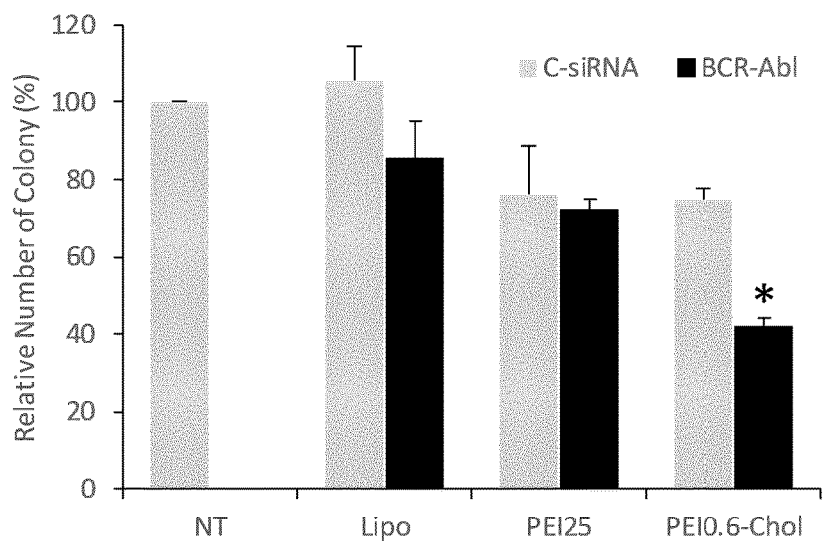
Figure 11B:
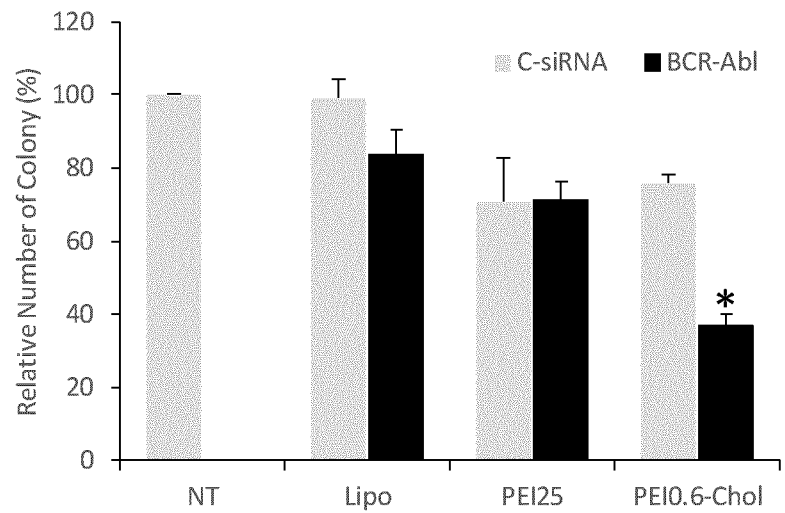

FIGS. 11A-B are graphs showing colony formation after 1 week (FIG. 11A) and 2 weeks (FIG. 11B) of K562-wt cells treated with BCR-Abl siRNA complexes. The results are summarized as relative numbers of colony compared to no treatment group (*p<0.01 vs C-siRNA treated group).

FIGS. 12A-D show flow cytometry cell distribution histograms on day-3 (FIG. 12A), summary of flow cytometry analysis for apoptotic cells on day-3 (FIG. 12B), flow cytometry cell distribution histograms on day-6 (FIG. 12C) and summary of flow cytometry analysis for apoptotic cells on day-6 (FIG. 12D) of K562-wt cells after the treatment with BCR-Abl-siRNA complexes. The results are summarized as PI- and Annexin V-positive cell population (late and early apoptosis, respectively) (*p<0.01 vs. C-siRNA treatment).

Figure 13:
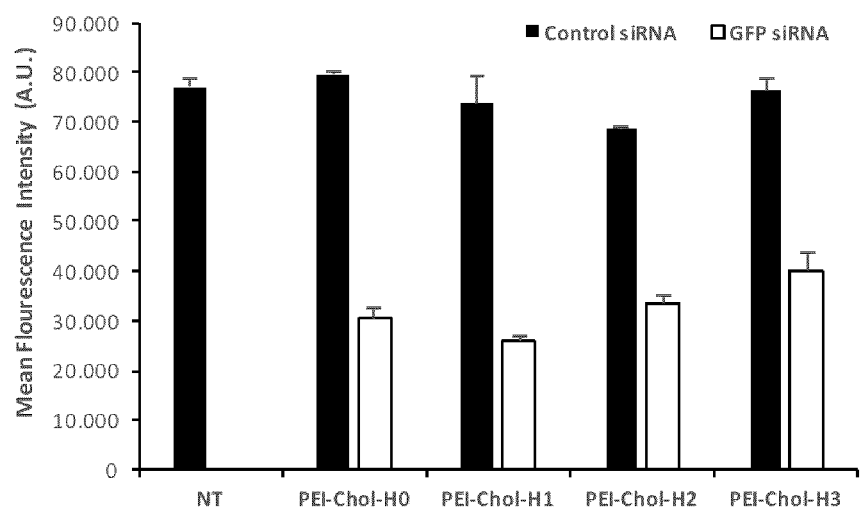

FIG. 13 is a graph showing inhibition of GFP expression in K562-GFP cells analyzed through flow cytometry after treatment with polymer/siRNA complexes for 3 days. The siRNA used was either control siRNA or GFP-specific siRNA. The polymers were substituted with cholesterol and histidine, with histidine substitution at various levels (H0, H1, H2 and H3 representing 0, 1, 2 and 3 histidine/PEI during synthesis, respectively). The analysis is summarized as the mean GFP expression compared to the non-treated cells (NT).

Figure 14:
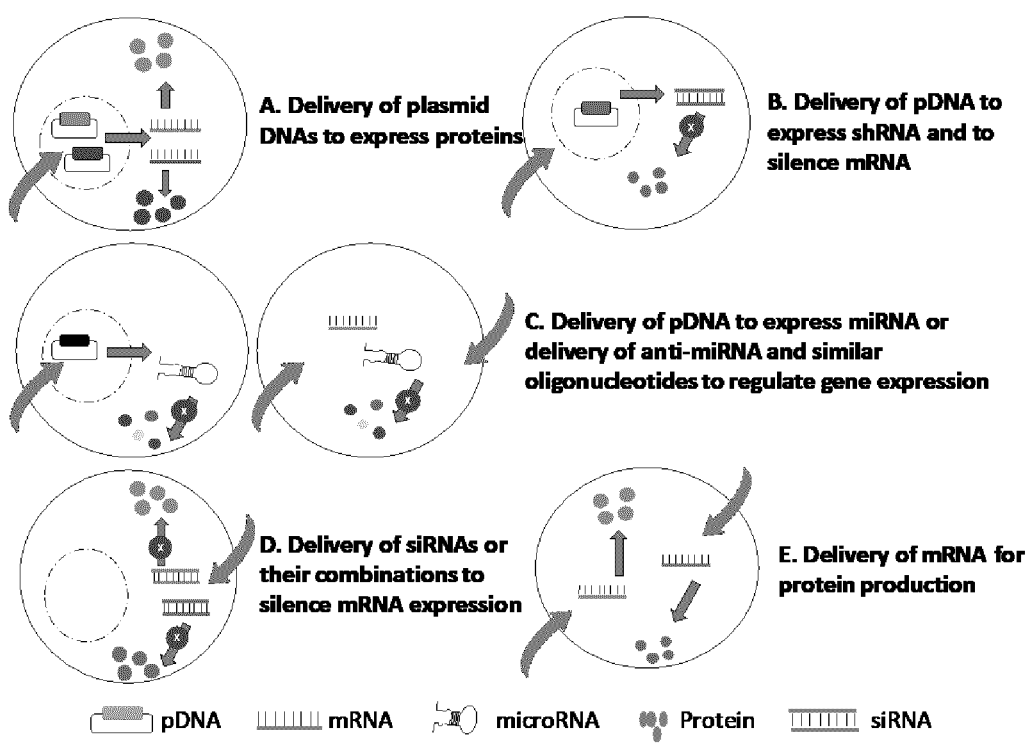

FIG. 14 shows various types of polynucleotides that can be delivered by the transfection reagents to the cells.

DETAILED DESCRIPTION OF PREFERRED EMBODIMENTS

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It must be noted that as used herein and in the appended claims, the singular forms "a," "an," and "the" include plural referents unless the context clearly dictates otherwise.

The present invention is directed to polymeric transfection reagents for delivery of nucleic acids to cells, pharmaceutical compositions comprising same, and methods of preparing and using same. As used herein, the term "polymeric transfection reagent" generally refers to a modified polymer which exhibits the ability to bind and deliver a nucleic acid to a cell. In the development of present invention, chemical modification of polymers was addressed since modified polymers may have potential as transfection reagents for nucleic acid delivery. Polymers, particularly those having relatively low molecular weights, are generally ineffective alone in their native state. However, modifying such polymers with lipidic groups enhances their affinity to lipid-based cell membranes. While unmodified polymers alone will bind strongly to nucleic acids, having lipid groups on the polymers enhances nanoparticle formation with nucleic acids and facilitates release of nucleic acids inside cells once internalized.

The polymeric transfection reagent of the present invention comprises a polymer and a lipid, and may also comprise the amino acid histidine. Suitable polymers include, but are not limited to, linear or branched forms of polyethylenimine (PEI) and other polyalkylimines including polypropylenimine; linear or branched forms of poly(amino acids) including polylysine, polyarginine, polyhistidine, and polyglutamate; poly(beta-amino acids) and poly(beta-amino esters); generally cationic amino acids containing peptides and polymers including the class of compounds generally known as 'cell-penetrating peptides' (e.g., TAT peptide); aminated polymers derived from water-soluble, uncharged polymers that are modified with particular amine compounds including natural amines such as lysine, histidine, spermine, etc., such as cellulosic materials, polyethylenglycol and polypropyleneglycol derivatives, polyesters including polyglycolic acid, polylactic acid, polycaprolactone, polyvinyl alcohol, albumin, gelatin, collagen and derivatives thereof, polyacrylates and derivatives thereof, polymetacrylates and derivatives thereof, dextran, cyclodextran, pullulan, chitosan, modified chitosan, carbon based structured materials such as fullerenes and carbon nanotubes, silica, gold, calcium, phosphate and similar inorganic particles; polyethylenimine derivatized with silica, polyethylenglycol, polypropyleneglycol, amino acids, dopamine, poly(2-dimethylaminoethyl methacrylate and derivatives thereof in combination with other polymers to create amphiphilic polymers; polyamidoamine derivatives with branched or dendritic architectures; and poly(N-(2-hydroxypropyl)methacrylamide) and derivatives thereof.

In one embodiment, the molecular weight of the polymer ranges from about 0.5 kDa to about 5 kDa. Suitable lipids include, but are not limited to, aliphatic lipids where the length of carbon changes from C3 (propionic acid) to C22 (behenic acid) including lauric acid, palmitic acid, stearic acid; unsaturated versions of aliphatic lipids including myristoleic acid (C14:1, cis-9), palmitoleic acid (C16:1, cis-9), and stearic acid (C18) derivatives, oleic acid (C18:1, cis-9), elaidic acid (C18:1, trans-9), linoleic acid (C18:2, cis-9,12) and linolenic acid (C18:3, cis-9,12,15); triglyceride including glyceryl tridecanoate, glyceryl tridodecanoate, glyceryl trimyristate, glyceryl trioctanoate, tripalmitin; cholesterol and its derivatives including cholic acid, deoxycholic acid, and cholanic acid; phospholipids including α-phosphatidylcholine, α-phosphatidylethanolamine, α-phosphatidyl-L-serine, α-phosphatidylinositol, α-phosphatidic acid, α-phosphatidyl-DL-glycerol, α-lysophosphatidylcholine, sphingomyelin, cardiolipin; synthetic lipidic compounds including diphytanoyl phosphatidylethanolamine (DPHPE), dioleoyl phosphatidylethanolamine (DOPE), dioleoyl phosphatidylcholine (DOPC), dilauryl phosphatidylethanolamine (DLPE), 1,2-distearoyl-sn-glycero-3-phosphatidylethanolamine (DSPE), and dimyristoyl phosphatidylethanolamine (DPME); multicyclic lipids and steroids including cholesterol, cholestanol, coprosterol, epicholestanol, epicholesterol, ergostanol, [alpha]-ergostenol, [beta]-ergostenol, [gamma]-ergostenol, ergosterol, 22,23-dihydroergosterol, stigmasterol, stigmastanol, (3[beta])-7-dehydrocholesterol, desmosterol, allocholesterol, 24-hydroxy cholesterol, 25-hydroxycholesterol, campesterol, [alpha]-sitosterol, [beta]-sitosterol, [gamma]-sitosterol, lumisterol, pyrocalciferol, isopyrocalciferol, azacosterol, neoergosterol, and dehydroergosterol.

The polymeric transfection reagent is amphiphilic in nature, having a combination of cationic and lipophilic groups which confer the ability to bind strongly to a nucleic acid by various mechanisms including, but not limited to, electrostatic and hydrophobic interactions, neutralize the anionic charge of the nucleic acid, and condense or package the nucleic acid into a form suitable for cell uptake. In one embodiment, the polymeric transfection reagent and nucleic acid are complexed to form a nanoparticle. Once inside the cell, the polymeric transfection reagent releases the nucleic acid to exert its specific effects. Such effects may include, but are not limited to, forced expression of desired genes to produce proteins; forced expression of desired genes to produce non-coding RNAs involved in gene regulation; silencing of desired mRNAs to stop production of proteins; silencing of desired regulatory RNAs to interfere with specific gene and mRNA expression; and expression of proteins from mRNA or other regulations of intracellular molecules by the delivered polynucleotides. These utilities of the polymeric transfection reagents are summarized in FIG. 14. Such delivery of nucleic acids will have various applications in the fields of medicine, biotechnology, and pharmacy.

As used herein, the term "nucleic acid" means a polynucleotide such as deoxyribonucleic acid (DNA), and, where appropriate, ribonucleic acid (RNA). The term should also be understood to include, as equivalents, analogs of either RNA or DNA. As used herein, the term "polynucleotide" is a linear sequence of ribonucleotides (RNA) or deoxyribonucleotides (DNA) in which the 3' carbon of the pentose sugar of one nucleotide is linked to the 5' carbon of the pentose sugar of another nucleotide. The deoxyribonucleotide bases are abbreviated as "A" deoxyadenine; "C" deoxycytidine; "G" deoxyguanine; "T" deoxythymidine; "I" deoxyinosine. Suitable nucleic acids for delivery by the polymeric transfection reagents of the present invention include, but are not limited to, DNA-based nucleic acids (e.g., plasmid DNA intended to code short hairpin RNA (shRNA), oligonucleotide, and antisense oligonucleotide), a peptide-nucleic acid (PNA), DNA-RNA chimeras, RNA-based nucleic acids (e.g., short interfering RNA, messenger RNA, non-coding RNAs such as micro-RNA).

In one embodiment, the nucleic acid comprises short interfering RNA. As used herein, the term "short interfering RNA" (abbreviated as "siRNA") means a double-stranded RNA molecule which interferes with the expression of a target gene with complementary nucleotide sequences by degrading mRNA after transcription or blocking mRNA translation, resulting in no translation of the targeted mRNA. In one embodiment, the target gene is selected from KIF11, FLT3, STAT3, STAT5A/B, RRM2, FLT1, RUNX1, Cyclin A2, Hsp70, p65, p100/52 (NfkB), HIF-1a, GFI-1B, Hsp27, Hsp32, CXCR4, CD44, Nucleoplasmin, an inhibitor of DNA binding (ID) protein, CD22, and MAX dimerization protein 3 (MDX3), or a fusion gene selected from AML1-ETO, BCR-ABL, BCR-JAK2, BCR-FGFR1, CEP110-FGFR1, ERG, EWS-FLI1, TEL-AML1, ETV6-ABL, ETV6-PDGFRB, ETV6-JAK2, ETV6-SYK2, EWS-ERG, FOP-FGFR1, HIP1-PDGFRB, H4-PDGFRB, MLL/ENL, MLLT10/AF10, MLL/AF9, a fusion gene comprising MLL, MYH11-CBFB, NUP98-NSD1, PAX3-FKHR, PML-RARA, RAB5-PDGFRB, RUNX1-RUNX1T1, TLS-FUS, or ZNF198-FGFR1.

Figure 1A:
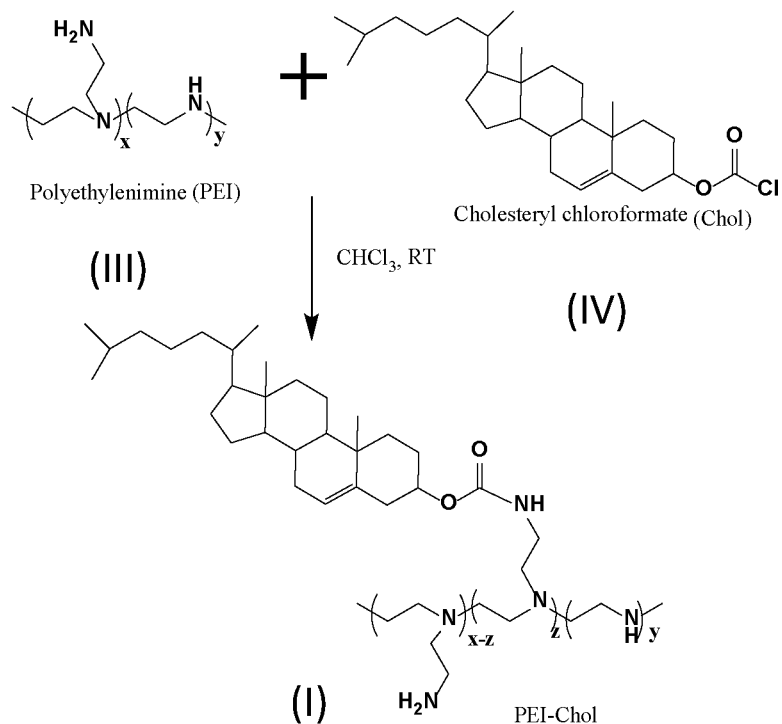
FIG. 1A is a scheme for the synthesis of cholesterol-grafted polyethyleneimine (PEI-Chol) polymers.

An exemplary polymeric transfection reagent of the invention is designated as "PEI-Chol" and shown in FIG. 1A. In one embodiment, the polymeric transfection reagent comprises the compound of formula (I):

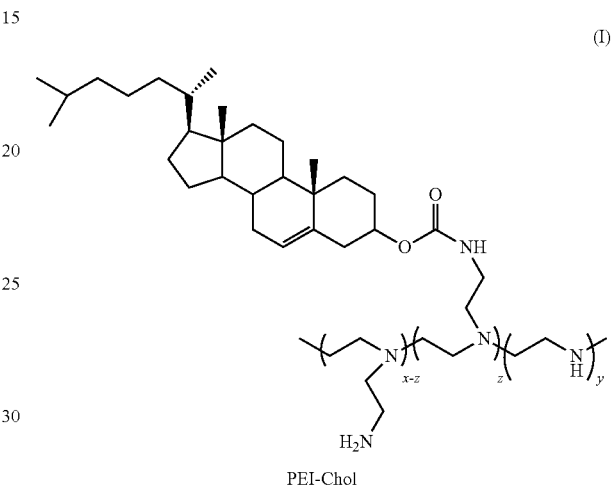

PEI-Chol

In one embodiment, the polymeric transfection reagent comprises the compound of formula (II):

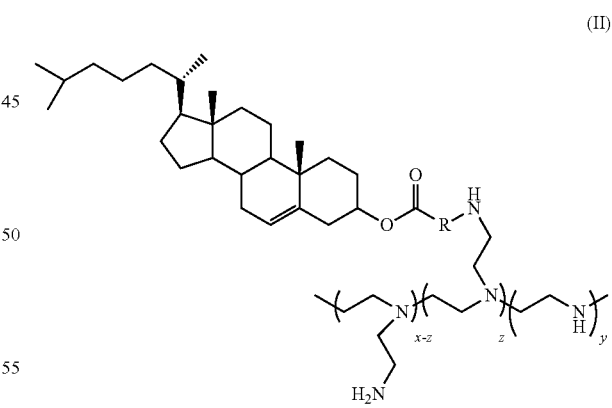

where R is a linker. In one embodiment, the linker comprises a spacer of 0<n<10 atoms and a cleavable or degradable chemical group. Non-limiting cleavable chemical groups include disulfides, thioesters, esters, phosphoesters, orthoesters, anhydrides, acetals, ketals, and carbonates.

In one embodiment, the polymeric transfection reagent comprises the compound of formula (IIa) which includes a linker R comprising a thioester:

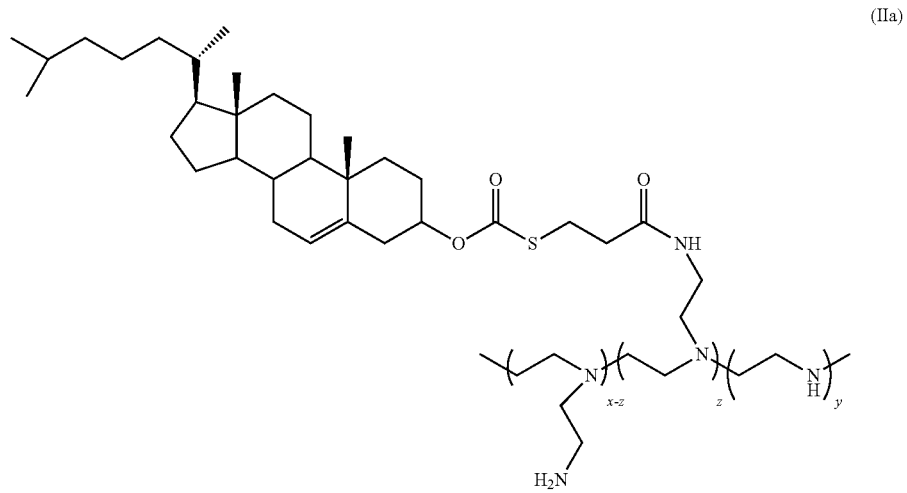

(IIa)

Figure 2A:
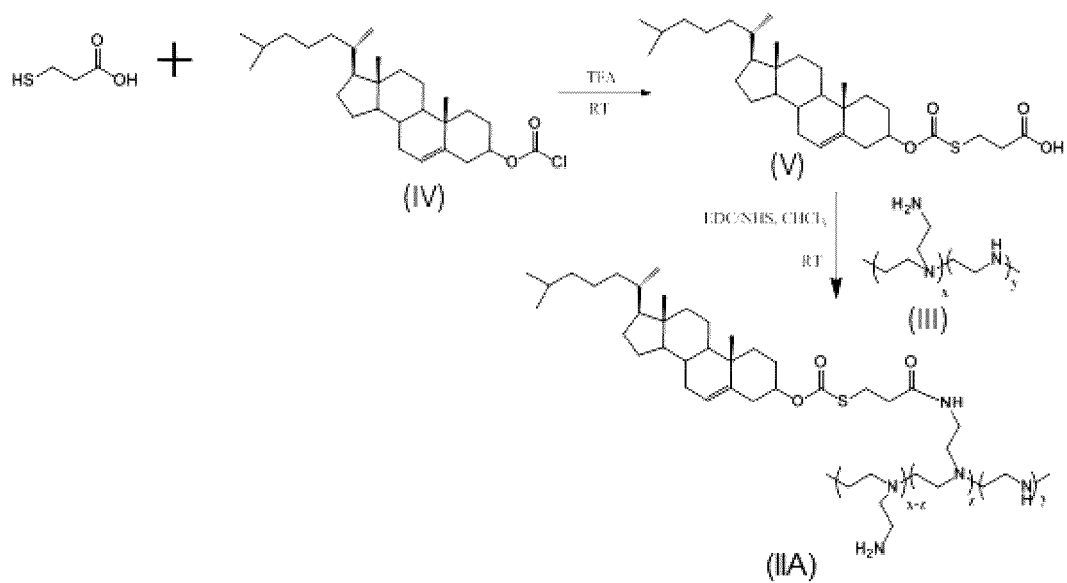
FIG. 2A is a reaction scheme between PEI (III) and activated cholesterol (IV) to obtain cleavable thioester PEI-Chol conjugate (IIB).

In one embodiment, the polymeric transfection reagent comprises the compound of formula (IIb) which includes a histidine:

In one embodiment, the present invention is directed to a process of preparing the polymeric transfection reagent comprising the compound of formula (I), (II), (IIa) or (IIb) from polyethylenimine, cholesterol and histidine as precursors (FIGS. 1A and 2A). As starting materials, polyethylenimine, cholesterol and histidine are non-toxic, inexpensive,

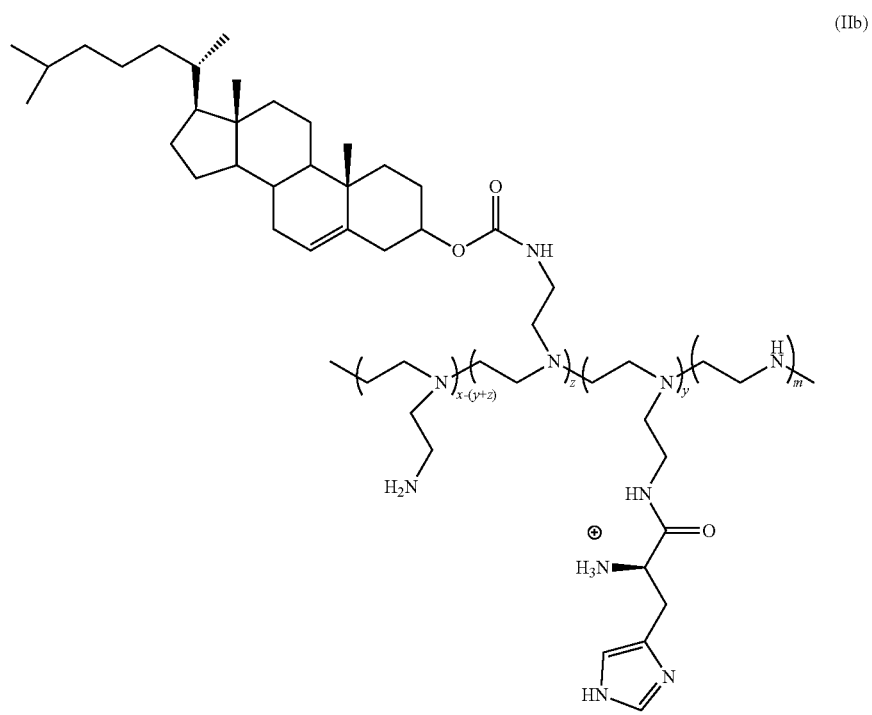

(IIb)

and readily available. Using non-toxic starting materials ensures that the resultant polymeric transfection reagent is biocompatible with highly sensitive cells. As used herein, the term "biocompatible" means generating no significant undesirable host response for the intended utility. Most preferably, biocompatible materials are non-toxic for the intended utility. Thus, for human utility, biocompatible is most preferably non-toxic and otherwise non-damaging to humans or human tissues.

As used herein, the term "polyethylenimine" (abbreviated as "PEI") means a polymer with a repeating unit composed of the amine group and two carbon aliphatic $CH_2CH_2$ spacers. The term is meant to include linear polyethylenimines containing all secondary amines; branched polyethylenimines which contain primary, secondary and tertiary amino groups; and hyperbranched, dendrimeric forms with primary, secondary and tertiary amino groups. In one embodiment, polyethylenimine is branched.

In one embodiment, polyethylenimine has a low molecular weight. As used herein, the term "low molecular weight" means a molecular weight ranging from about 0.5 kDa to about 5 kDa, more preferably from about 0.6 kDa to about 2.0 kDa, and most preferably 0.6 kDa to about 1.2 kDa. The low molecular weight reduces the strength of the binding between the polymer and the nucleic acid, thus ensuring that the nucleic acid can be easily and readily released once inside a cell. The substituted lipid groups also reduce the binding strength for the same reason.

In one embodiment, polyethylenimine comprises the compound of formula (III):

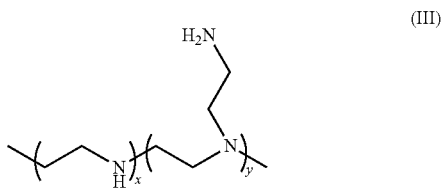

(III)

In one embodiment, cholesterol is in the form of cholesteryl chloroformate comprising the compound of formula (IV)

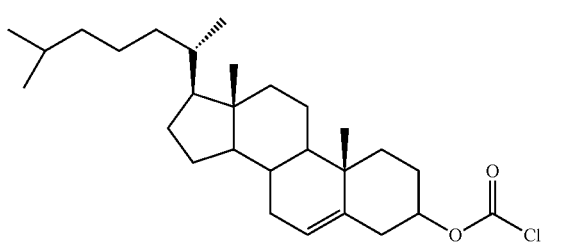

(IV)

In one embodiment, histidine is an α-amino acid in the form of the compound of formula (V):

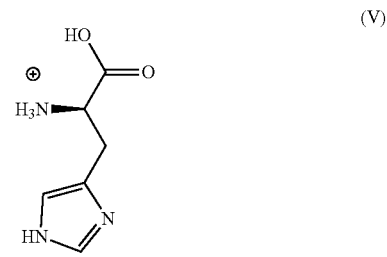 [SMILES: N[C@H](Cc1c[nH]cn1)C(=O)O]

(V)

As described in Examples 1-2, the steps of the process are as follows. In one embodiment, polyethylenimine and cholesteryl chloroformate are used as starting materials to produce the polymeric transfection reagent (I) via N-acylation. Briefly, polyethylenimine and cholesteryl chloroformate are dissolved separately in anhydrous chloroform and cooled. Triethylene amine is added to the polyethylenimine solution. The cholesteryl chloroformate solution is added to the polyethylenimine solution and left overnight at room temperature. The resulting polymer transfection reagent (I) is precipitated in diethyl ether and dried under vacuum. The structure of the polymer transfection reagent (I) is confirmed by examination of one or more spectra including, but not limited to, proton NMR spectra (FIG. 1B), infrared spectra, mass spectra, carbon spectra, and the like. The polymeric transfection reagent (I) may be examined for its potential for siRNA binding, unpacking, and digestion using a dye exclusion and an agarose gel retardation assay (Example 3).

In one embodiment, cholesterol is in the form of cholesteryl chloroformate end-capped with propionic acid via a thioester linkage, comprising the compound of formula (VI):

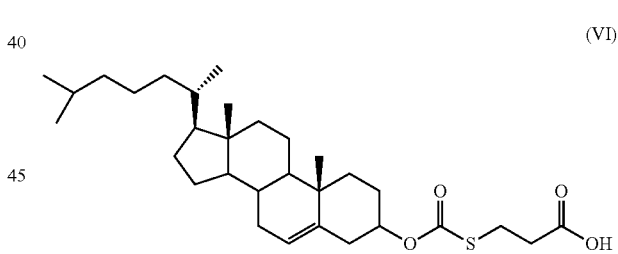

(VI)

Figure 2B:
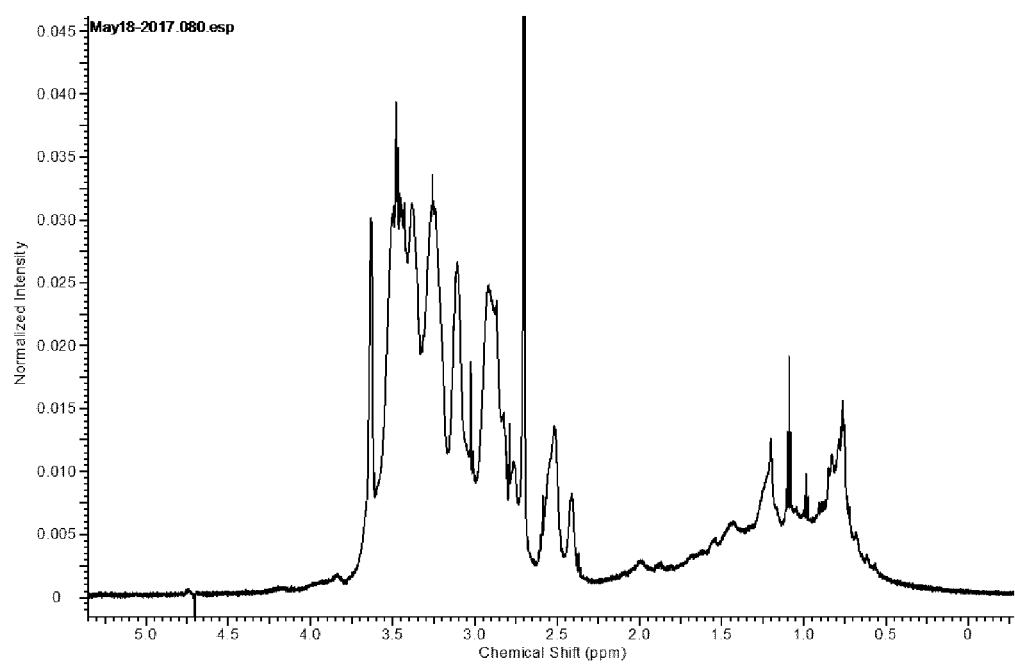
FIG. 2B is a $^1$H-NMR spectrum of a PEI-Chol polymer with a cleavable thioester linkage.

In one embodiment, polyethylenimine, cholesteryl chloroformate, and 3-mercaptopropionic acids are used as starting materials to produce biodegradable polymeric transfection reagent (II). One typical example of this group is cholesterol grafted polyethylenimine via a thioester linkage (IIa). Thioester linkage (—S—CO—) is generated onto cholesterol by its coupling with 3-mercaptopropionic acid (MPA). Briefly, cholesterol and MPA are dissolved separately in trifluoroacetic acid. MPA solution is added to the cholesterol solution. The final product is precipitated in hexane and dried under vacuum. The carboxyl end-capped cholesterol is grafted onto branched polyethylenimines through 1-ethyl-3-(3-dimethylamino-propyl)carbodiimide (EDC)/N-hydroxysuccinimide (NHS) activation (FIG. 2A). Briefly, carboxyl end-capped cholesterol is activated with EDC/NHS and added to the polyethylenimine solution. The mixture is stirred overnight at room temperature. The crude product is precipitated using diethyl ether and dried under vacuum. The structural composition of polymeric transfection reagent (IIa) may be confirmed by examination of one or more spectra including, but not limited to, $^1$H-NMR spectroscopy (FIG. 2B), infrared spectra, and mass spectra. The polymeric transfection reagent (IIa) may be examined for siRNA binding, unpacking and digestion using a dye exclusion and an agarose gel retardation assay (Example 3).

In one embodiment, polyethylenimine, cholesteryl chloroformate, and histidine are used as starting materials to produce intermediate lipopolymeric reagent (IIb). Histidine is grafted onto branched PEI in chloroform through 1-ethyl-3-(3-dimethylamino-propyl) carbodiimide (EDC)/N-hydroxysuccinimide (NHS) activation. Briefly, to the reaction mixture of polyethylenimine and cholesteryl chloroformate (as explained in synthesis of compound I) activated histidine is added. The ratio of PEI to histidine is varied between 0, 1, 2 and 3 mol:mol ratio. The mixture is stirred overnight at room temperature. The crude product is precipitated using diethyl ether and dried under vacuum. The composition of polymeric transfection reagent (IIb) may be confirmed by examination of one or more spectra including, but not limited to, $^1$H-NMR spectroscopy, infrared spectra, and mass spectra. The polymeric reagent (IIb) may be examined for nucleic acid binding, unpacking and protection using a dye exclusion and agarose gel retardation assay (Example 3).

The steps of the process for preparing the polymeric transfection reagent-siRNA complex (hereinafter referred to as a "nanoparticle") are as follows. Briefly, the polymeric transfection reagent in water or an aqueous-based buffer is diluted with a sodium chloride solution, and siRNA is added to generate the polymeric transfection reagent-siRNA complex (Example 3). The use of aqueous-based buffers in this process generates the polymeric transfection reagent-siRNA complex in the form of a nanoparticle, eliminating the need to use organic solvents during nanoparticle formation.

The nanoparticle can be analyzed to determine its physical and chemical properties (Example 4). In one embodiment, the nanoparticle has a hydrodynamic size ranging from about 50 nm to about 200 nm, and preferably from about 100 nm to about 200 nm. Such hydrodynamic sizes are considered sufficiently small so as to be suitable for effective cellular uptake. In one embodiment, the nanoparticle has a surface charge or $\zeta$-potential which has been enhanced in the range of about +10 mV to about +35 mV.

The utility of the nanoparticle may be confirmed by testing in various ways including, for example, in vitro cell culture assays using appropriate host cells. As used herein, the term "host cell" refers to any suitable type of cell which can be transfected with the nanoparticle of the present invention. The nanoparticle can be introduced into the host cell by various techniques well known in the art. As used herein, the term "transfection" refers to the uptake of foreign DNA or RNA by a cell by any means practicable. A cell has been transfected when an exogenous nucleic acid has been introduced inside the cell membrane. The uptake of the nucleic acid results in a transient transfectant, regardless of the means by which the uptake is accomplished. Those skilled in the art can select a particular host cell line that is best suited to assess silencing expression of a gene of interest.

Suitable host cells include, but are not limited to, anchorage-dependent, anchorage-independent, and easy-to-grow cells typically used in the biotechnology industry for production of various biochemicals including proteins. As used herein, the term "anchorage-dependent cell" means a cell which needs contact and anchorage to a stable surface in order to grow, function, and divide. As used herein, the term "anchorage-independent cell" means a cell which has lost the need for anchorage dependence and has transformed or become neoplastic, and thus is typically difficult to transfect. Examples of anchorage-independent cells include, but are not limited to, a leukemia cell and more particularly, a chronic myeloid leukemia cell; tumor cells that are shed to systemic circulation ("circulating tumor cells"); and lymphocytes typically found in circulating blood, bone marrow and other parts of the lymphatic system such as the spleen and lymph nodes. The ability of the improved polymeric transfection reagents of the present invention to function as effective siRNA carriers to target anchorage-independent cells is a considerable advantage.

Uptake, delivery of siRNA to the host cell, and silencing of gene expression (as observed for example, by inhibition of cell growth, induction of apoptosis) may be assessed as described for instance, in Examples 5-12. As described in these Examples, cholesterol-grafted low molecular weight polyethylenimines were generated for siRNA delivery to target BCR-Abl in chronic myeloid leukemia model K562 cells. Post-transcriptional gene silencing was studied with a reporter gene (green fluorescent protein, GFP) virally incorporated into K562 cells, as well as the endogenous BCR-Abl oncogene and Kinesin Spindle Protein (KSP) involved in cell division and proliferation. The specificity of the cholesterol-conjugated polyethylenimines for siRNA delivery to chronic myeloid leukemia cells was explored by using polyethylenimines with different lipid substituents and attachment-dependent cells. The results showed that lower molecular weight polyethylenimines grafted with cholesterol were most effective in silencing target genes and inhibiting cell growth via induction of apoptosis.

The nanoparticle may also be evaluated in vivo using animal models. For example, the nanoparticle may be administered to mice having leukemia by various routes including, but not limited to, orally, subcutaneously, inhalationally, intravenously, or intraperitoneally in appropriate dosage forms and fixed dosages. Assessments following treatment with the nanoparticle may include, but are not limited to, pharmacokinetics, biodistribution, uptake, leukemia cell response, toxicity, histopathology, and host morbidity.

In one embodiment, the invention comprises pharmaceutical compositions comprising the nanoparticle of the present invention in combination with one or more pharmaceutically acceptable carriers, targeting ligands, anti-fouling agents, or combinations thereof.

As used herein, the term "carrier" means a suitable vehicle which is biocompatible and pharmaceutically acceptable, including for instance, liquid diluents which are suitable for administration. Those skilled in the art are familiar with any pharmaceutically acceptable carrier that would be useful in this regard, and therefore the procedure for making pharmaceutical compositions in accordance with the invention will not be discussed in detail.

As used herein, the term "targeting ligand" means a molecule capable of binding to a desired (target) molecule. Use of a targeting ligand allows for delivery of therapeutic agents to specific cells and tissues to enhance the efficacy of therapy for a disease. Non-limiting examples of targeting ligands include an antibody or fragment thereof against a cell surface protein (for example, CD34, CD11, etc.), an aptamer from an oligonucleotide, a peptide, a protein, a polysaccharide, a small molecule (for example, a vitamin), general ligands that can bind to cell surface receptors (e.g., transferrin, folate, RGD and similar peptides, etc.), or ligands that bind to tissues having diseased cells (e.g., bisphosphonate class of compounds that bind to bone marrow). Target cell surface molecules include, but are not limited to, JL1, CA19-9, CD2, CD3, CD5, CD11, CD19, CD20, CD33, CD34, CD38, CD44, CD52, CD74, CD96, CD99, CD117, CD135, CD166, CD184, CLL1, CXCR4, folate or folic acid, LFA-1, MMP-2, MMP-9, PTK7, sigma, transferrin, biotin, lectin, PD-1, and SMALF7. The targeting ligand can be incorporated into the nanoparticle by chemical means where the targeting ligand is anchored to the surface of the nanoparticle by covalent linkages; or by using an anchor that penetrates and becomes immobilized in the nanoparticle. Non-limiting examples of reagents which help to keep the targeting ligand embedded in the nanoparticle include polyethyleneglycol or cholesterol linkers.

As used herein, the term "anti-fouling agent" means a substance that prevents detriment of function. The anti-fouling agent may be incorporated onto the surface of the nanoparticle via physical (e.g., electrostatic) and chemical (e.g., covalent bonding) methods. In one embodiment, the anti-fouling agent is an anionic anti-fouling agent. In one embodiment, the anti-fouling agent comprises a hydrophilic polymer selected from polyethylene glycol, hyaluronic acid, alginate, heparin, heparin sulfate, chondroitin sulfate, dermatan sulfate, or keratin sulfate. The anti-fouling agent potentially enhances the half-life of the nanoparticle after administration to a patient. Consequently, it can increase bio-distribution, bio-availability, tissue interactions and other pharmacokinetic behavior of the nanoparticle since hydrated "sheath" coating can prevent protein adsorption, opsonization and cell-mediated phagocytosis.

As used herein, the term "pharmaceutically acceptable" means a substance which does not significantly interfere with the effectiveness of the nanoparticle, and which has an acceptable toxic profile for the host to which it is administered. Suitably, the pharmaceutical compositions may be in the form of liquids and solutions suitable for administration in liquid dosage forms as appropriate and in unit dosage forms suitable for easy administration of fixed dosages. The dosage of the nanoparticle depends upon many factors that are well known to those skilled in the art, for example, the type and pharmacodynamic characteristics of the nanoparticle; age, weight and general health condition of the host; nature and extent of symptoms; any concurrent therapeutic treatments; frequency of treatment and the effect desired.

In one embodiment, the invention comprises a kit for preparing and administering the pharmaceutical compositions. In one embodiment, the kit comprises a polymeric transfection reagent; a nucleic acid; and one or more pharmaceutically acceptable carriers, targeting ligands, anti-fouling agents, or combinations thereof. In one embodiment, the polymeric transfection reagent comprises the compound having the formula (I), (II), (IIa), or (IIb). The components may be contained within any container suitable for storage or administration of medicines and other therapeutic compositions. For example, the components may be contained within a sealed and sterilized plastic or glass container having a defined volume such as a vial, ampule, syringe, cartridge, bottle, or intravenous (IV) bag. Different types of vials can be used to contain the components including, e.g., clear and opaque (e.g., amber) glass or plastic vials. The kit may further comprise one or more suitable reagents (for example, aqueous-based buffer), utensils, and vessels for combining the components to form the pharmaceutical composition; an applicator (for example, a syringe) for administering the pharmaceutical composition to the subject; and instructions for preparation and administration of the pharmaceutical composition.

Certain embodiments of the invention thus relate to methods and uses of the nanoparticle to deliver siRNA to a cell and silence expression of a gene of interest. The nanoparticle may be used to reduce incidence of, reduce, treat, diminish, or prevent a disease or disorder in a subject where it is of benefit to silence expression of a gene of interest by, for example, inhibiting cell growth, and inducing apoptosis. In one embodiment, the disease is leukemia, and more particularly, chronic myeloid leukemia (CML). Therapeutic uses of the nanoparticle in diseases or disorders, methods of prevention or treatment using the nanoparticle, and uses of the nanoparticle to prepare medicaments for therapeutic use are also contemplated in certain embodiments of the invention. Certain embodiments relate to the therapeutic use of the nanoparticle in humans.

In one aspect, the invention provides a method of treating, preventing, or ameliorating a disease or disorder in a subject, comprising administering to the subject an effective amount of the nanoparticle or a composition comprising same. As used herein, the term "disease" includes, but is not limited to, any disease commonly referred as cancer and arising from non-attachment dependent cells such as, for example, chronic myeloid leukemia, acute myeloid leukemia, chronic lymphocytic leukemia, acute lymphocytic leukemia, hairy cell leukemia, meningeal leukemia, and other plasma cell neoplasms. The disease may originate from fusogenic gene fragments leading to cancerous growth in the case of myeloma, multiple myeloma, lymphoma, brain cancer, bladder cancer, breast cancer, melanoma, skin cancer, epidermal carcinoma, colon and rectal cancer, lung cancer, non-Hodgkin lymphoma, Hodgkin lymphoma, Sezary Syndrome, endometrial cancer, pancreatic cancer, kidney (renal cell) cancer, prostate cancer, leukemia thyroid cancer, head and neck cancer, ovarian cancer, hepatocellular cancer, cervical cancer, sarcoma, gastric cancer, gastrointestinal cancer, uterine cancer, and other proliferative diseases.

As used herein, the term "subject" means a human or other vertebrate. As used herein, the term "effective amount" means any amount of a formulation of the nanoparticle useful for treating, preventing, or ameliorating a disease or disorder upon administration. An effective amount of the composition provides either subjective relief of symptoms or an objectively identifiable improvement as noted by the clinician or other qualified observer. As used herein, the terms "treating," "preventing," and "ameliorating" refer to interventions performed with the intention of alleviating the symptoms associated with, preventing the development of, or altering the pathology of a disease, disorder or condition. Thus, in various embodiments, the terms may include the prevention (prophylaxis), moderation, reduction, or curing of a disease, disorder or condition at various stages. In various embodiments, therefore, those in need of therapy/treatment may include those already having the disease, disorder or condition and/or those prone to, or at risk of developing, the disease, disorder or condition and/or those in whom the disease, disorder or condition is to be prevented.

In one embodiment, an effective amount of the nanoparticle or a composition comprising same can be administered to the subject in conjunction with one or more drugs used to treat the disease to provide complementary activity. In one embodiment, the disease is a proliferative disorder affecting blood cells. Careful selection of conventional drug therapy combined with the nanoparticle and compositions of the present invention may enhance the therapeutic response to either treatment approach. Acceptable drug therapies, particularly for disorders related to blood cancers and other proliferative diseases, can be found in the literature, for example at the website of USA National Institute of Health. Suitable drugs include, but are not limited to, Alemtuzumab, Arsenic Trioxide, Asparaginase, Azacitidine, Bendamustine Hydrochloride, Belinostat, Bleomycin, Blinatumomab, Bortezomib, Bosutinib, Brentuximab, Vedotin, Busulfan, Carmustine, Carfilzomib, Cladribine, Clofarabine, Chlorambucil, Cyclophosphamide, Cytarabine, Dasatinib, Daunorubicin Hydrochloride, Dacarbazine, Daratumumab, Decitabine, Denileukin Diftitox, Doxorubicin Hydrochloride, Elotuzumab, Fludarabine Phosphate, Imatinib Mesylate, Hydroxyurea, Ibrutinib, Idarubicin Hydrochloride, Idelalisib, Intron A (Recombinant Interferon Alfa-2b), Ixazomib Citrate, Lenalidomide, Lomustine, Mercaptopurine, Mechlorethamine Hydrochloride, Methotrexate, Nelarabine, Nilotinib, Nivolumab, Obinutuzumab, Ofatumumab, Omacetaxine Mepesuccinate, Pamidronate Disodium, Panobinostat, Pegaspargase, Pembrolizumab, Plerixafor, Pomalidomide, Ponatinib Hydrochloride, Pralatrexate, Prednisone, Procarbazine Hydrochloride, Rituximab, Romidepsin, Thalidomide, Thioguanine, Tositumomab, Vincristine Sulfate, Venetoclax, Vinblastine Sulfate, Vorinostat, and Zoledronic Acid.

Embodiments of the present invention are described in the following Examples, which are set forth to aid in the understanding of the invention, and should not be construed to limit in any way the scope of the invention as defined in the claims which follow thereafter.

Example 1—Materials

Branched polyethylenimine (PEI) of 25 kDa (PEI25), 2.0 kDa (PEI2.0) [50%, w/v in water], cholesteryl chloroformate (Chol), methylthiazolyldiphenyl tetrazolium bromide (MTT), and heparin sodium salt were from Sigma-Aldrich Corporation (St. Louis. MO). The solution of PEI2.0 was lyophilized to remove water just before conjugation reactions. Branched 1.2 kDa PEI of (PEI1.2) and 0.6 kDa PEI (PEI0.6) were obtained from Polysciences, Inc. (Warrington, PA, USA). SYBR Green I was purchased from Cambrex Bio Science (Rockland, MD). The scrambled siRNA (C-siRNA), and 5'-carboxyflourescein (FAM)-labeled scrambled siRNA (FAM-siRNA) were obtained from Invitrogen (Burlington, ON). GFP-siRNA (GFP-22) was obtained from Qiagen (Toronto, ON), a custom-synthesized BCR-Abl siRNA (5'-GCAGAGUUCAAAAGCCCTT-3'; SEQ ID NO: 1) and 3'-TTCGUCUCAAGUUUUCGGG-5; SEQ ID NO: 2) was obtained from Integrated DNA Technologies, Inc. (IDT; Coralville, IA). Cell culture reagents were obtained from Invitrogen (Grand Island, NY). Lipofectamine™ 2000 was obtained from Invitrogen. Annexin V-FITC Apoptosis Kit I was purchased from BD Biosciences (San Jose, CA). The solvents were obtained from Sigma-Aldrich.

Example 2—Polymer Synthesis and Characterization

Cholesterol (Chol) derivatives of PEI2.0, PEI1.2 and PEI0.6 were prepared via N-acylation using cholesteryl chloroformate (FIG. 1A). Chol (2.22 mM) and PEI (2.22 mM) were separately dissolved in anhydrous chloroform and cooled on ice bath for 30 min. To the PEIs solution, 100 μL of triethylene amine (TEA) was added and it was stirred under ice bath. Chol solution was added dropwise to the PEI solution under stirring and the reaction mixture was left stirring overnight at room temperature. The crude product of Chol grafted PEIs (PEI-Chol) was precipitated (3×) in ice cold diethyl ether and dried under vacuum for 48 hr. A separate polymer library of saturated aliphatic lipids grafted PEIs was synthesized using the same protocol (Table 1).

TABLE 1

Summary of polymers synthesized with aliphatic lipid substituents.

| Polymer ID | Feed ratio (mol/mol) | Calculated NMR (mol/mol) |
| --- | --- | --- |
| PEI0.6-PA | 4.0 | 1.75 |
| PEI0.6-StA | 4.0 | 2.55 |
| PEI1.2-PA | 4.0 | 1.64 |
| PEI1.2-StA | 4.0 | 2.63 |
| PEI2-PA | 6.0 | 2.46 |
| PEI2.0-StA | 6.0 | 2.14 |

Cholesterol (Chol) grafted polyethylenimine via thioester linkage (IIa) was prepared via EDC/NHS activation (FIG. 2A). First, thioester linkage (—S—CO—) was generated onto cholesterol by its coupling with mercaptopropionic acid (MPA). Briefly, cholesterol (449 mg, ~1.0 mmol) and MPA (332 μL, 2.5 mmol) were dissolved separately in TFA (1.0 mL). MPA solution was added dropwise to cholesterol solution and the reaction mixture was stirred for 3 hr at room temperature. The carboxyl end-capped cholesterol was collected by precipitation (3×) in ice cold hexane and dried under vacuum for 48 hr. The carboxyl end-capped cholesterol was then grafted onto branched polyethylenimines through EDC/NHS activation. Briefly, carboxyl end-capped cholesterol (0.2 mmol in 20 mL $CHCl_3$) was activated (1 hr) with EDC (0.3 mmol in 1 mL $CHCl_3$) and NHS (0.4 mmol in 1 mL methanol). It was then added to polyethylenimines solution (0.1 mmol in 100 mL $CHCl_3$). The mixture was stirred overnight at room temperature. The crude product was precipitated (3×) in ice cold diethyl ether and dried under vacuum for 48 hr. Two different saturated aliphatic lipids [PA: Palmitoyl chloride (C16), Stearoyl chloride (C18)] were grafted onto PEIs of molecular weight 0.6, 1.2 and 2.0 kDa, via N-acylation using different feed ratios (mol/mol). The extent of lipids substitution was quantified using the integral values of characteristic proton resonance peaks of lipids vs. PEIs in the $^1$H-NMR spectra. The structural composition of the polymers was thus elucidated through $^1$H-NMR spectroscopy (Bruker 300 MHz, Billerica, MA) using TMS as an internal standard in $D_2O$ and Chol grafting was quantified. The histidine conjugated polymers were obtained as follows: to the reaction mixture of PEI1.2 and cholesteryl chloroformate (as explained in procedure to synthesize compound I) activated histidine (with EDC/NHS) is added. The mixture is stirred overnight at room temperature. The crude product is precipitated using diethyl ether and dried under vacuum. The structural composition of polymeric transfection reagent (IIb) may be confirmed by examination of one or more spectra including, but not limited to, $^1$H-NMR spectroscopy, infrared spectra, and mass spectra.

Example 3—siRNA Binding, Complexes Unpacking and Digestion Study

The siRNA binding capacity of PEI-Chol polymers, unpacking of resultant complexes, and serum digestion of siRNA complexes were elucidated by a dye exclusion and an agarose gel retardation assay. For binding study, polymer solutions (1.0 μg/μL) were diluted with NaCl solution (0.15

M) in microcentrifuge tubes to obtain a final concentration of 0 to 0.045 µg/µL polymer. 2 µL of siRNA (0.3 µg/µL in water) was added to each tube (triplicate) and gently vortexed to obtain complexes of 0 to 1.5 polymer/pDNA ratios (w/w). After 30 min of incubation at room temperature, the complexes were diluted with 100 µL SYBR Green I (1× in TAE buffer). Complex solutions (100 µL) were loaded into black 96-well plates and the fluorescence values were measured ($\lambda_{EX}$=485, $\lambda_{EM}$=527 nm) with a microplate fluorometer. The amount of free siRNA in the complexes was quantified using blank siRNA as reference control. The binding capacity of the polymers was expressed as $BC_{50}$: polymer:siRNA ratio required to bind 50% of siRNA. To investigate the unpacking dynamics of polymer/siRNA complexes, an anionic challenge was carried out using heparin. Polymer/siRNA (w/w=5) complexes were prepared in 0.15 M NaCl at room temperature and heparin solution was added to each complex to yield a final concentration of 0 to 60 U/mL heparin and incubated for 1 hr at room temperature, followed by the dye exclusion assay. The unpacking of the complexes in this anionic environment was expressed as $DC_{50}$: amount of heparin (U/mL) required for 50% complex dissociation. To study the digestion of siRNA in complexes, polymer/siRNA (w/w=5) complexes were prepared at room temperature, and incubated in fresh rat serum (final concentration 50%) for 24 hr at 37° C. The nuclease activity was inactivated by heating the solutions at 90° C. for 15 minutes in the presence of 25 mM EDTA, after which the siRNA in complexes was released by adding 4 µL of 1450 heparin U/mL. The heat treated tubes were centrifuged to remove any solid formed. The complexes were mixed with the loading buffer (4 µL, 6×) and then loaded into agarose gel (0.8%, in 1×TAE buffer) containing EtBr (1 µg/mL). The gel was electrophoresed for 45 min at 120 mV and the siRNA bands were visualized under UV (Alpha Imager EC). The amount of intact siRNA recovery was quantified and expressed as a percentage of a reference standard.

Example 4—Physicochemical Characterization

Hydrodynamic size and surface charge (zeta ($\xi$)-potential) of the complexes were assayed in $ddH_2O$ through dynamic light scattering (DLS) and electrophoretic light scattering (ELS) using Zetasizer Nano-ZS (Malvern, UK). The polymer/siRNA complexes (2.5, 5.0 and 10.0 w/w) were prepared at room temperature and then diluted to 1 mL with $ddH_2O$ for measurements. The morphology and distribution of the complexes were studied through transmission electron microscopy (TEM) using formvar-carbon coated Copper Grids. The complex (10 w/w) solution (5 µL) was dropped onto the grids and dried with tissue paper. It was stained with 10 µL uranyl acetate (2%) for 5 min and mounted for measurement. TEM images were taken using Philips 410 operated at 80 kV at accelerating voltage.

Example 5—Cell Culture

BCR-Abl positive CML cells, wild-type K562 (K562-wt), green fluorescence protein expressing K562 (K562-GFP) and attachment-dependent breast cancer MDA-MB-231 cells were used as model cells. The stable GFP expression in K562 cells was generated by transfection with a retroviral vector containing GFP genes. Cells were maintained in RPMI (CML cells) or DMEM (MDA-231) medium containing FBS (10%), penicillin (100 U/mL) and 100 µg/ml streptomycin in a humidified atmosphere of 95 air/5% $CO_2$.

Example 6—Uptake of siRNA in K562 Cells

In vitro siRNA uptake was studied through flow cytometry using K562-wt cells. The complexes were prepared by incubating the polymers with FAM-siRNAs in RPMI medium and added to cells in complete medium (at 60 nM). Commercially available Lipofectamine™ 2000 and branched PEI25 were used as reference carriers. Complexes of these carriers with siRNAs were formulated in the same medium and at indicated compositions (ratios). Briefly, 7.92 µL (10 µM) of FAM-siRNA was mixed with 13.3 µL (1 mg/mL) of polymer in 300 µL RPMI to yield complexes with the ratio of 12 (w/w). After incubation for 30 min at room temperature, complexes were directly transferred to 48-well plate. Then, cells (300 µL of 100,000 cells/mL) were transferred to the wells containing the complexes. Cells were incubated in humidified atmosphere at 37° C. for 24 hr. and collected in microcentrifuge tubes (1.5 mL) and centrifuged (1400 rpm) for 5 min, washed (2×) with HBSS (pH 7.4) and finally fixed with formalin (3.7% in HBSS). The FAM-positive cell population was quantified by Beckman Coulter QUANTA™ SC Flow Cytometer using FL1 channel (3000 events/sample).

Example 7—GFP Silencing in K562-GFP Cells

The K562-GFP cells were treated with polymer/GFP-siRNA complexes and incubated for 72 hr in a humidified atmosphere at 37° C. For first time point (day-3), 300 µL of the cells was processed for flow cytometry, and remaining 100 µL of cell suspension was mixed with 300 µL fresh media and incubated for next time point (day-6 and -9). The cells were processed similarly at day-6. To quantify the extent of GFP silencing, cells were processed for flow cytometry and GFP levels in the cells were quantified using FL1 channel. The results are expressed as the percentage of reduction in GFP fluorescence and percentage of cells that displayed reduced GFP levels as compared to untreated K562-GFP cells.

Example 8—BCR-Abl Silencing by RT-PCR

The silencing of BCR-Abl in CML cells (K562-wt and K562-GFP cells) after transfecting with PEI-Chol/BCR-Abl-siRNA complexes was studied through real-time quantitative Polymerase Chain Reaction (RT-qPCR). Complexes (200 µL, ratio 12, w/w, final siRNA concentration of 60 nM) were transferred into 24-well plates on top of which 600 µL of cells suspension (100,000 cells/mL) was added and incubated for 3 days in a humidified atmosphere and 95% air/5% $CO_2$. 600 µL of cells was processed on day 3 to assess BCR-Abl mRNA levels and 200 µL of cell suspension was sub-cultured for next time point (day-6) by mixing with 600 µL fresh medium. The cells were also harvested on day-9 for BCR-Abl levels. Cells were collected in tubes, spun-down, washed (2×) with HBSS and total RNA was isolated using TRIzol reagent (Invitrogen). For each sample, two microgram of total RNA was reverse transcribed into cDNA using M-MLV reverse transcriptase (Invitrogen) according to the manufacturer's instructions. OligodT as well as random primers were used for cDNA synthesis (25). Primers used to amplify β-actin (Forward: 5'-CCA CCC CAC TTC TCT CTA AGG A-3'; SEQ ID NO: 3), Reverse: 5'-AAT TTA CAC GAA AGC AAT GCT ATC A-3' (SEQ ID NO: 4) and GAPDH (Forward: TCA CTG TTC TCT CCC TCC GC; SEQ ID NO: 5), Reverse: 5'-TAC GAC CAA ATC CGT TGA CTC C-3'; SEQ ID NO: 6) as the endogenous housekeeping genes and BCR-Abl (Forward: 5'-CAT TCC GCT GAC CAT CAA TAA G-3'; SEQ ID NO: 7, Reverse: 5'-GAT GCT ACT GGC CGC TGA AG-3'; SEQ ID NO: 8) (27) were designed by the NCBI Primer-BLAST (http://www.ncbi.nlm.nih.gov/tools/primer-blast/), and were supplied by IDT. To follow the fluorescence intensity, 2×SYBR Green master mix with ROX as a passive reference dye (MAF Center, University of Alberta) was used. A total of 10 µL volume containing 5 µL of 2× master mix SYBR Green, 1 µL of 10 µM forward primer, 1 µL of 10 µM reverse primer and 3 µL of cDNA template (5 ng/µL) from each sample (in triplicate) were transferred to Fast Optical 96-well plate. Reaction mixtures were heated for 2 min at 95° C. followed by 40 cycles of denaturation step (15 s at 95° C.) and an annealing/elongation step (1 min at 60° C.) using StepOne-Plus Real-Time PCR System. The gene expression results by RT-qPCR was analyzed by $2^{-\Delta\Delta CT}$ method and presented as a relative quantity of mRNA transcripts of BCR-Abl against β-actin and GAPDH. As a negative control, template cDNA was omitted from the RT-qPCR reaction.

Example 9—Target gene (BCR-Abl and KSP) Silencing and Cell Growth Inhibition In vitro growth inhibition of K562-wt and K562-GFP cells was assessed after treatment with polymer/siRNA complexes, where a control siRNA and a custom synthesized BCR-Abl siRNA were used to form complexes. Polymer/siRNA complexes at ratios of 6, 9 and 12 (w/w) were prepared in RPMI medium at room temperature and directly added to the cells. Briefly, 7.92 µL (10 µM) of FAM-siRNA was mixed 13.3 µL (1 mg/mL) of polymer in 300 µL RPMI to get the complexes of ratio 12, w/w. After 30 min incubation at room temperature, complexes (100 µL) were directly transferred to 48-well plate. Then, 300 µL (100,000 cells/mL) of cells was added on top of the wells and then incubated in the humidified atmosphere of 95% air/5% $CO_2$. The cell growth was assessed on day-3, day-6 and day-9 via the MTT (3-(4,5-dimethylthiazol-2-yl)-2,5-diphenyl-tetra-zolium bromide) assay. For first time point (day-3), 300 µL of the cells was processed for MTT assay and the remaining 100 µL was mixed with fresh media (300 µL) and incubated for next time points (day-6 and -9) where cells were partitioned under similar conditions as on day-3. For the MTT assay, MTT reagent (5 µg/µL in HBSS) was added to the wells to get final concentrating 1.0 µg/µL and incubated for 3 hr. The cells were collected in tubes (1.5 mL) and centrifuged at 1400 rpm for 5 min., washed (2×) with HBSS (pH 7.4) and finally formazan crystal was dissolved in DMSO (200 µL). The optical density was measured in a universal microplate reader at 2=570 nm.

Example 10—Colony Formation Assay

To monitor stem cell proliferation and colony formation, K562-wt cells were transfected with BCR-Abl siRNA complexes and colony formation was monitored after 1 and 2 weeks. Cells were transfected with the indicated polymer/BCR-Abl siRNA complexes (polymer:siRNA ratio 12 and 60 nM siRNA concentration) in a 24 well-plate. One day after transfection, 200 cells of each groups were mixed with 1 mL methylcellulose medium (Metholcult H4230; STEM-CELL Technologies) containing 10% IMDM (STEMCELL Technologies) and seeded in 35 mm culture dishes. The numbers of colonies were counted 1 and 2 weeks after incubation, as described in Zhou et al. (2008).

Example 11—Apoptosis (Annexin V) Assay

Induction of apoptosis with polymer/siRNAs complexes was studied in K562-wt cells using Annexin staining. Polymer/siRNAs complexes (with control and BCR-Abl siRNAs) of ratios 12 (w/w) were prepared in microcentrifuge tubes. Complexes (100 µL in triplicate) were directly transferred to 48-well plates and then 300 µL (100,000 cells/mL) of K562 cells were added to the complexes. After 3 days incubation in a humidified atmosphere, 100 µL of the cells were sub-cultured by mixing with 300 µL fresh medium for day-6 study and same process was done for day-9 study. The remaining 300 µL cell suspension was labeled with the Annexin kit according to the manufacturer's instructions. Cells were collected into microcentrifuge tubes, spun-down, washed (2×) with cold HBSS and finally aliquoted ($1×10^5$ cells) into a 100 µL binding buffer (1×). The labeling fluorochromes, FITC-Annexin V (5.0 µL) and Propidium Iodide (PI, 5.0 µL) were added to the cell suspension and incubated in the dark for 15 min at room temperature. It was diluted with 400 µL HBSS and analyzed through a BD LSR Fortessa flow cytometer (Franklin Lake, NJ). The Annexin-V positive and PI-positive cell population was quantified for each sample.

Example 12—Statistical Analysis

The results were reported as the mean±STD (n=3). Student's two-tailed t-test assuming equal variance was used to determine statistical significance ($p<0.05$) of the experimental. The levels of statistical significance (p values) are indicated for the appropriate Figures accordingly.

Example 13—Results

Figure 1B:
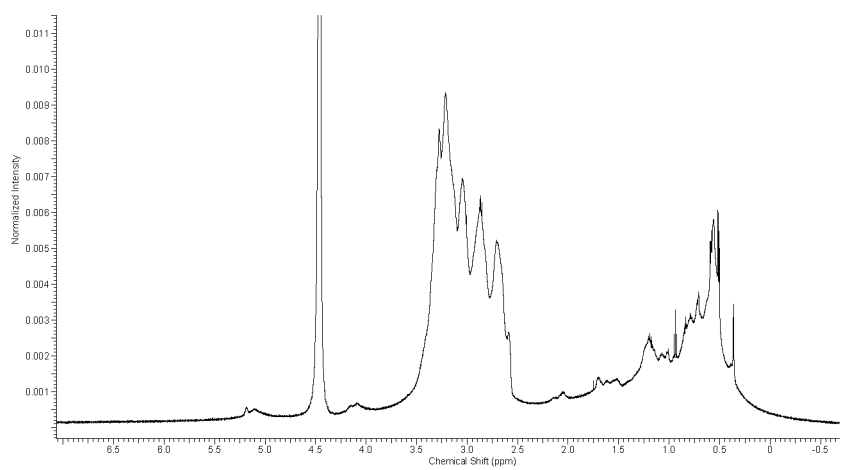
FIG. 1B is a $^1$H-NMR spectrum of a PEI-Chol polymer.

Discussed below are results obtained by the inventors in connection with the experiments of Examples 1-12.
Polymer Synthesis and Characterization Cholesterol-grafted PEIs (PEI-Chol) were synthesized through N-acylation (FIG. 1A). The $^1$H-NMR spectrum of PEI-Chol showed typical PEI and Chol proton resonances peaks (δ ~2.5-3.7 ppm and δ ~0.25-2.5 ppm, respectively) (FIG. 1B). A distinct resonance peak arising from Chol=CH— proton was observed at δ ~5.25 ppm. Chol substitution was quantified based on the peak areas corresponding to the two peaks and the results are summarized in Table 2.

TABLE 2

Summary of lipid substitution on resultant polymers

| Polymer ID | Chol/PEI, mol/mol (feed ratio) | Chol/PEI, mol/mol (from $^1$H-NMR) |
|---|---|---|
| PEI0.6-Chol1 | 1.0 | 0.54 |
| PEI0.6-Chol2 | 2.0 | 1.08 |
| PEI1.2-Chol1 | 1.0 | 0.65 |
| PEI1.2-Chol2 | 2.0 | 1.14 |
| PEI1.2-Chol3 | 3.0 | 2.21 |
| PEI2.0-Chol1 | 1.0 | 0.85 |
| PEI2.0-Chol2 | 2.0 | 1.45 |
| PEI2.0-Chol4 | 4.0 | 2.36 |

For each type of PEI backbone, Chol substitution was in proportion to the Chol/PEI feed ratio. Similarly, Chol substitution was also proportional to polymer molecular weight, with larger polymers having higher Chol substitutions. The highest Chol grafting (2.36 Chol/PEI) was obtained on PEI2 from the Chol/PEI2 feed ratio 4.0, and it corresponded to consumption of 15.8% primary amines. PEI-Chol polymers obtained from higher feed ratios (other than the ones listed in Table 2) were insoluble in water and were not further studied.

siRNA Binding of Polymers and Polyplex Properties

Figure 3A:
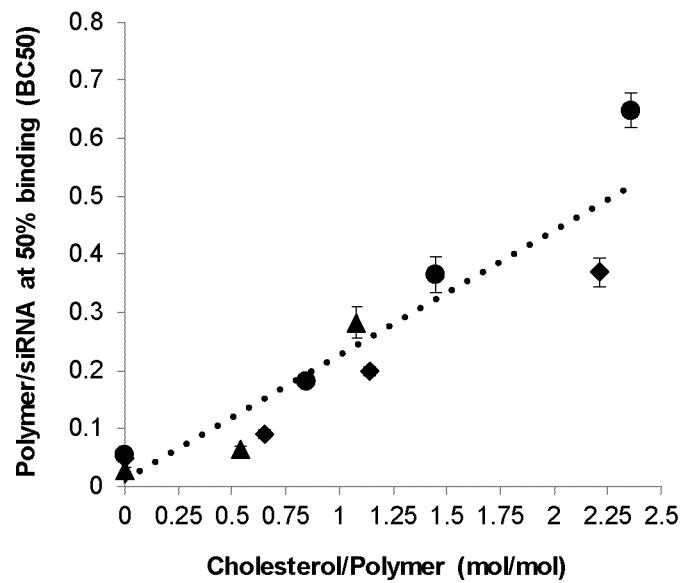
FIG. 3A is a graph showing siRNA binding capacity ($BC_{50}$; polymer/siRNA weight ratio at 50% siRNA binding) of PEI-Chol polymers as a function of Chol substitution.
Figure 3B:
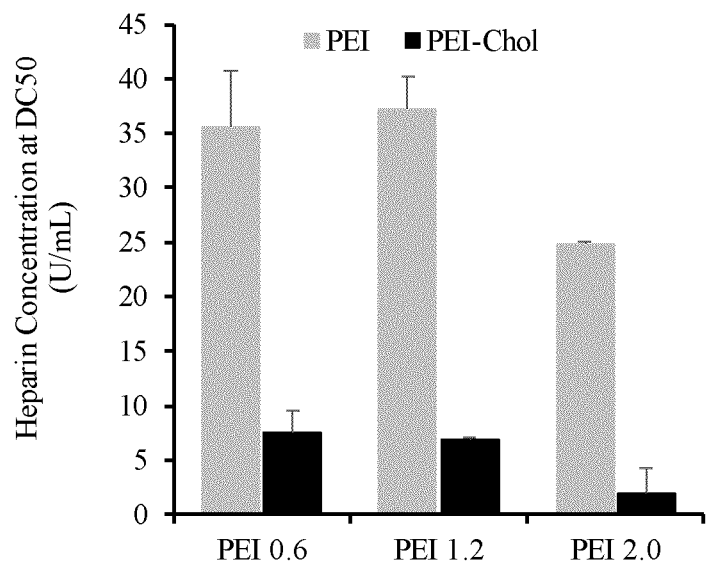
FIG. 3B is a graph showing $DC_{50}$ (heparin concentration (U/mL) for dissociation of 50% of complexes) for PEI/siRNA and corresponding PEI-Chol/siRNA complexes (*p<0.01); and comparing native PEIs to Chol substituted PEI in each molecular weight backbone.
Figure 3C:
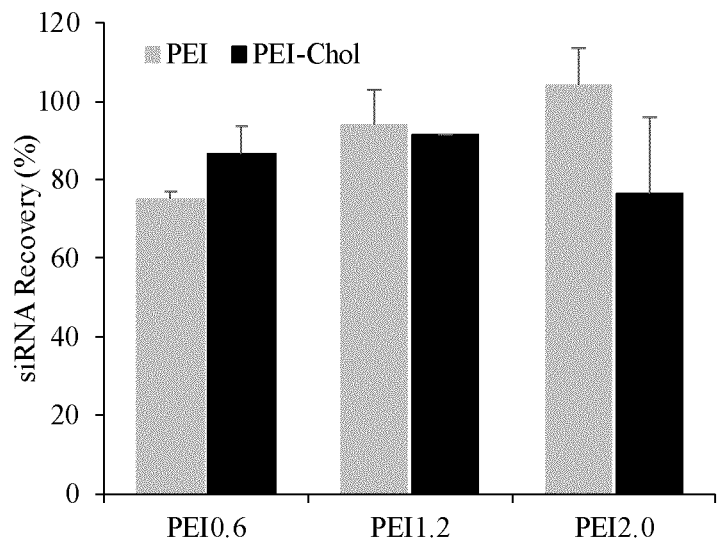
FIG. 3C is a graph showing recovery of intact siRNA from complexes incubated in fresh rat serum for 24 hr at 37° C. by agarose gel electrophoresis, and prepared by using native PEIs and their highest Chol substituted derivatives.

To investigate the binding capacity as a result of Chol substitution, electrophoretic mobility shifts assay was employed. The binding capacity of the parent polymers (PEI0.6, PEI1.2 and PEI2.0), as determined by $BC_{50}$ (i.e., weight ratio required for 50% binding of siRNA) was almost identical among the polymers ($BC_{50}$~0.05), while it was increased up to 2.36 with PEI2.0-Chol4, the highest Cholesterol-substituted polymer (FIG. 3A). The stability of PEI-Chol/siRNA complexes was examined by comparing the integrity of complexes from parent PEIs vs. highest Chol-substituted PEIs upon anionic (heparin) challenge. The dissociation constant, $DC_{50}$ (i.e., heparin concentration required for 50% dissociation) of PEI0.6, PEI1.2 and PEI2.0 ranged from 24.8 to 35.5 U/mL, while it was significantly ($p<0.005$) decreased to 1.9 to 7.6 U/mL with the PEI-Chol polymers (FIG. 3B). The decreased binding capacity combined with increased sensitivity to heparin dissociation may have implications on protection of siRNAs in polyplexes against serum nucleases. PEI/siRNAs and PEI-Chol/siRNA complexes were thus incubated with fresh rat serum for 24 hr and the complexes were dissociated with heparin for analysis of siRNA integrity with EMSA. Both types of polymers were able to protect 80 to 90% of siRNA, with no apparent effect of Chol substitution (FIG. 3C).

Figure 3D:
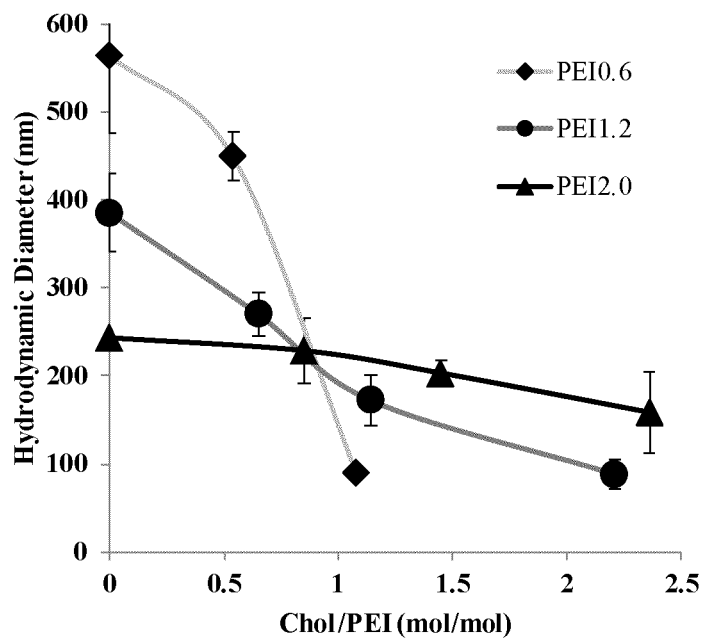
FIG. 3D is a graph showing hydrodynamic size (nm) of the complexes (polymer/siRNA ratio=12, w/w) prepared with PEI-Chol polymers.
Figure 3E:
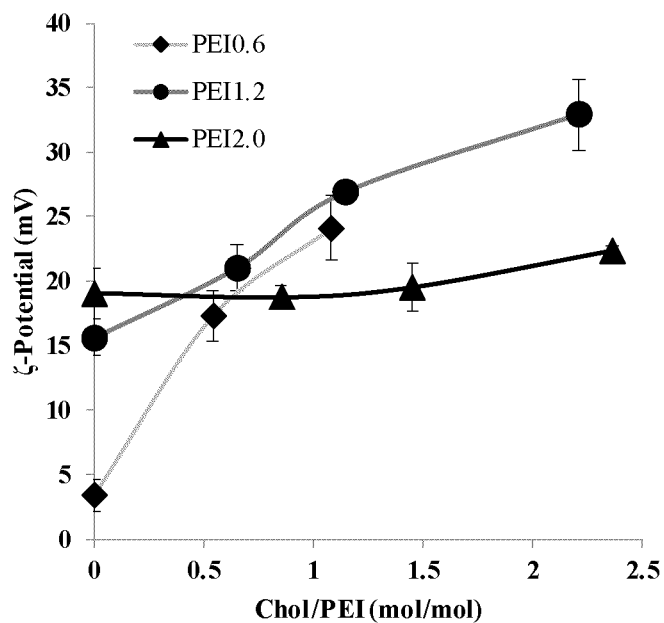
FIG. 3E is a graph showing zeta (ζ) potential (mV) of the complexes (polymer/siRNA ratio=12, w/w) prepared with PEI-Chol polymers.
Figure 3F:
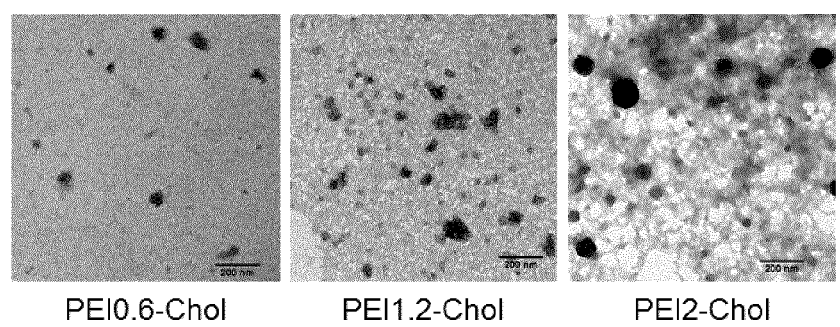
FIG. 3F are transmission electron microscopy (TEM) micrographs of the complexes (polymer/siRNA ratio=12, w/w) prepared with PEI-Chol polymers.

The results indicate that binding capacity of PEI-Chol was inversely proportional to amount of Chol substitution: higher substitution resulted in higher $BC_{50}$. The reason behind this phenomenon is stearic effect generated by the bulky hydrophobic moieties. Due to weak binding capacity, these polymers generate complexes of higher $DC_{50}$, indicating higher dissociation sensitivity. The increased dissociation sensitivity of the complexes was not due to reduced amines on PEIs, since the extent of amine consumption was typically ~15% of the total primary amines. In spite of the increased dissociation sensitivity, PEI-Chol displayed sufficient siRNA protection capability against serum nucleases (given by 80-90% recovery of intact siRNA), making the polymers suitable candidates for nucleic acid delivery under physiological conditions. The hydrodynamic size and surface charge of the complexes was examined by dynamic light scattering. As with aliphatic lipid substitutions on PEI, the impact of Chol substitution both on the size and surface charge of polyplexes was also along similar lines (FIGS. 3D-E). The hydrodynamic size of the complexes from Chol-substituted PEI0.6 and PEI1.2 was significantly decreased to ~100 nm, but the impact of Chol-substitution on PEI2.0 was marginal. Likewise, surface charge was significantly increased to approximately +35 mV while using Chol derivatives of smaller PEIs, but the effect on PEI2.0 was minor. TEM micrographs of the complexes mimicked the results of dynamic light scattering studies, where the particles sizes were in the 50 to 100 nm range in each case (FIG. 3F). The sizes of PEI2.0-Chol4/siRNA complexes were largest among the study groups, but all obtained sizes were considered small enough for effective cellular uptake. In cationic polymers, complexation between the polymer and siRNAs is followed by condensation, which is further assisted by hydrophobic-hydrophobic interactions among the lipid moieties in cationic polymers, resulting in further stabilization and formation of compact nanoparticles (15). Therefore, a proper hydrophobicity-hydrophilicity balance is essential to get compact nanoparticles and ~1 Chol substitution per PEI0.6 and PEI1.2 appeared to be sufficient. In PEI2.0-Chol, the higher Chol substitution may substantially inhibit complexation and aggregation (due to steric hindrance), which was not enough to reduce the size of complexes formed by the native PEI2.0.

Cellular Uptake of Complexes

Figure 4A:
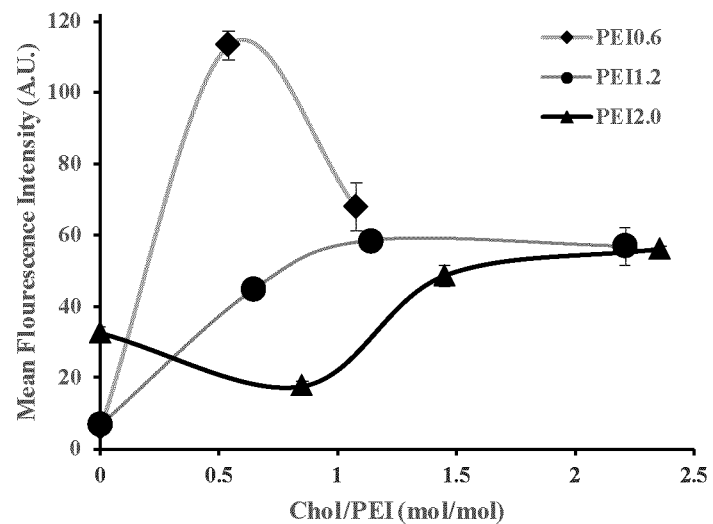
FIGS. 4A-B are graphs showing cellular uptake of complexes in wild-type K562 (K562-wt) cells as determined by flow cytometry analysis summarized as the mean fluorescence intensity per cell (FIG. 4A) and FAM-siRNA positive cell population (FIG. 4B).
Figure 4B:
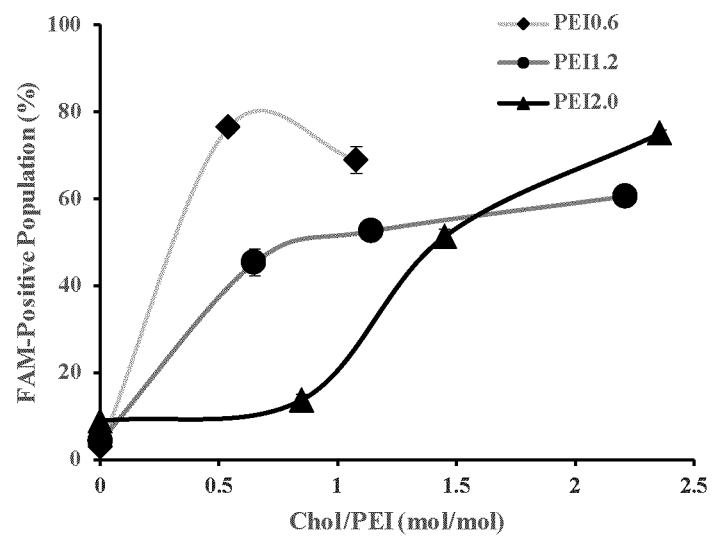

It is essential to understand the cellular uptake of polyplexes to gain better insight into the overall efficacy of carriers. Cellular delivery of siRNA by Chol-PEIs was assayed in K562 cells using FAM-labeled siRNA (FAM-siRNA) and using complexes prepared at polymer:siRNA ratio 12:1. Uptake efficacy is summarized in FIGS. 4A-B, as mean fluorescence intensity per cell as well as percentage of siRNA-positive cell population. Chol substitution significantly ($p<0.005$) enhanced cellular uptake efficacy of all MW PEIs, indicating the beneficial effect of modification. The lowest MW PEI0.6 benefited the most from Chol substitution, by giving the most effective polymer among the lipopolymers. Polymer/FAM-siRNA complexes of all PEI-Chol polymers showed higher (>75%) or comparable (~50%) efficacy to the broadly effective 25 kDa branched PEI (PEI25).

Silencing of GFP Reporter Gene

Figure 5A:
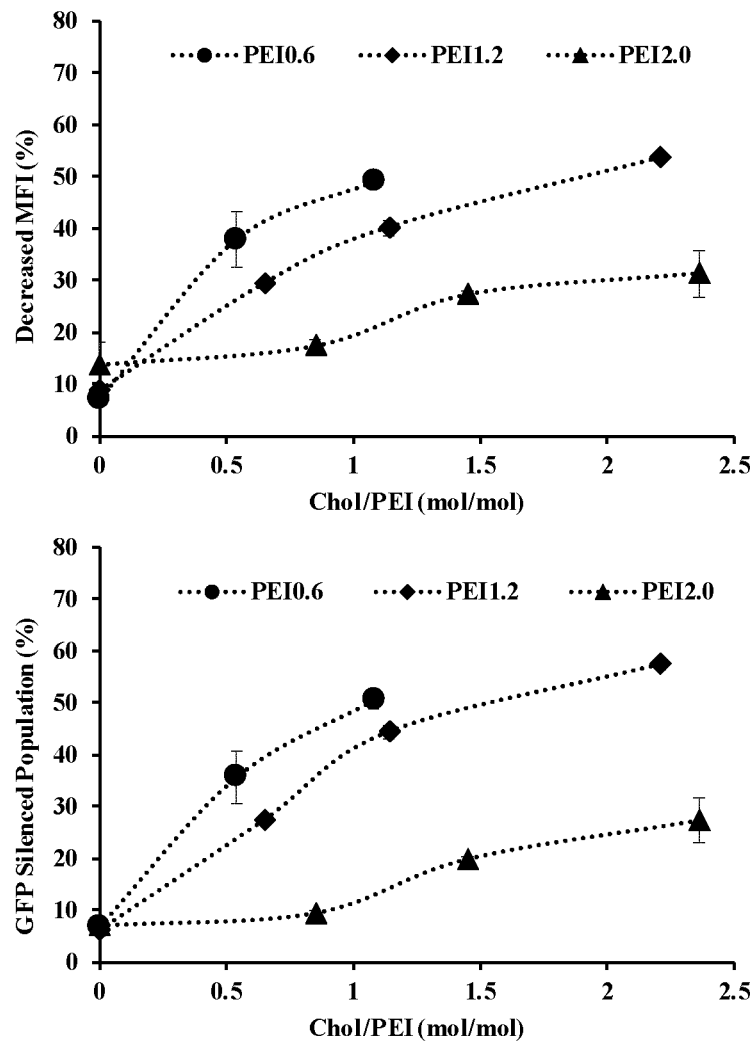
FIG. 5A-C are graphs showing GFP silencing efficiency in GFP-expressing K562 cells (K562-GFP) of the Chol-substituted PEIs as the function of cholesterol substitution, with the cells being incubated for different time points (day 3, day 6, day 9) and as determined by flow cytometry analysis summarized as decreased mean GFP fluorescence per cell and as percentage of GFP-silenced cell population.
Figure 5B:
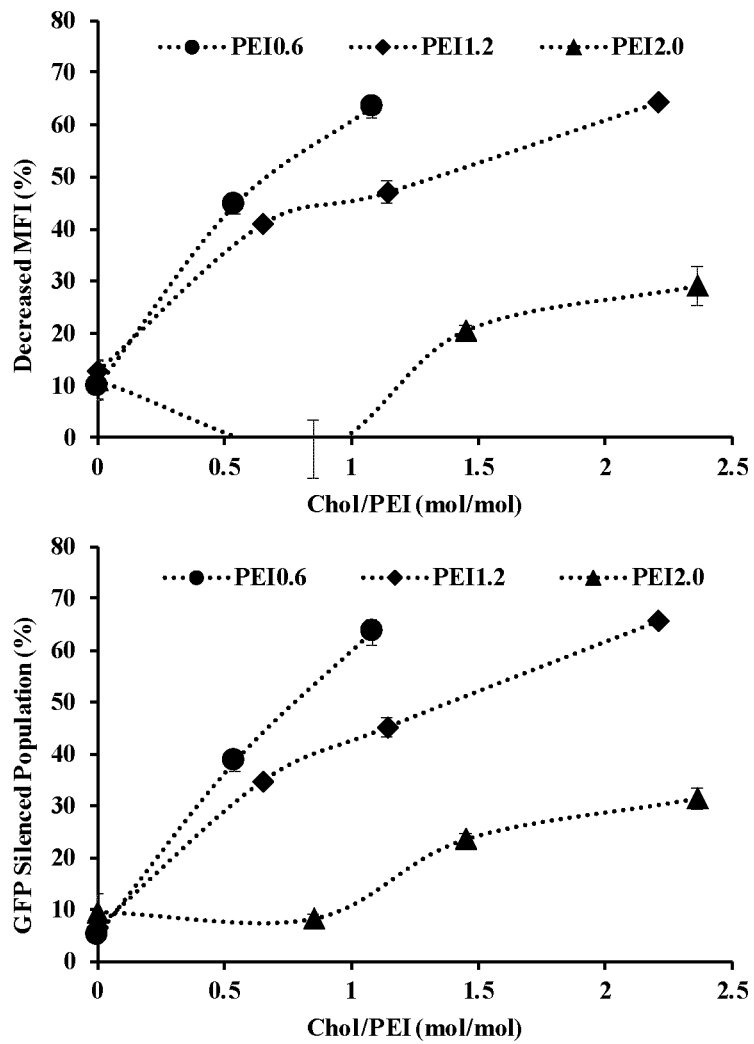
Figure 5C:
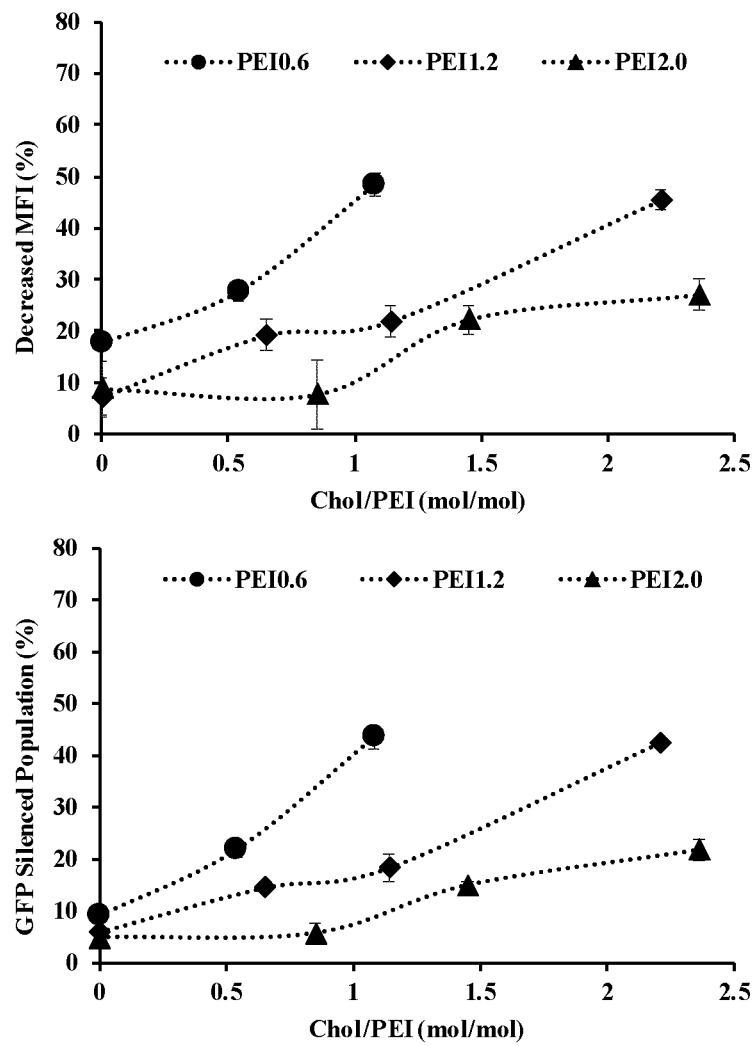
Figure 6A:
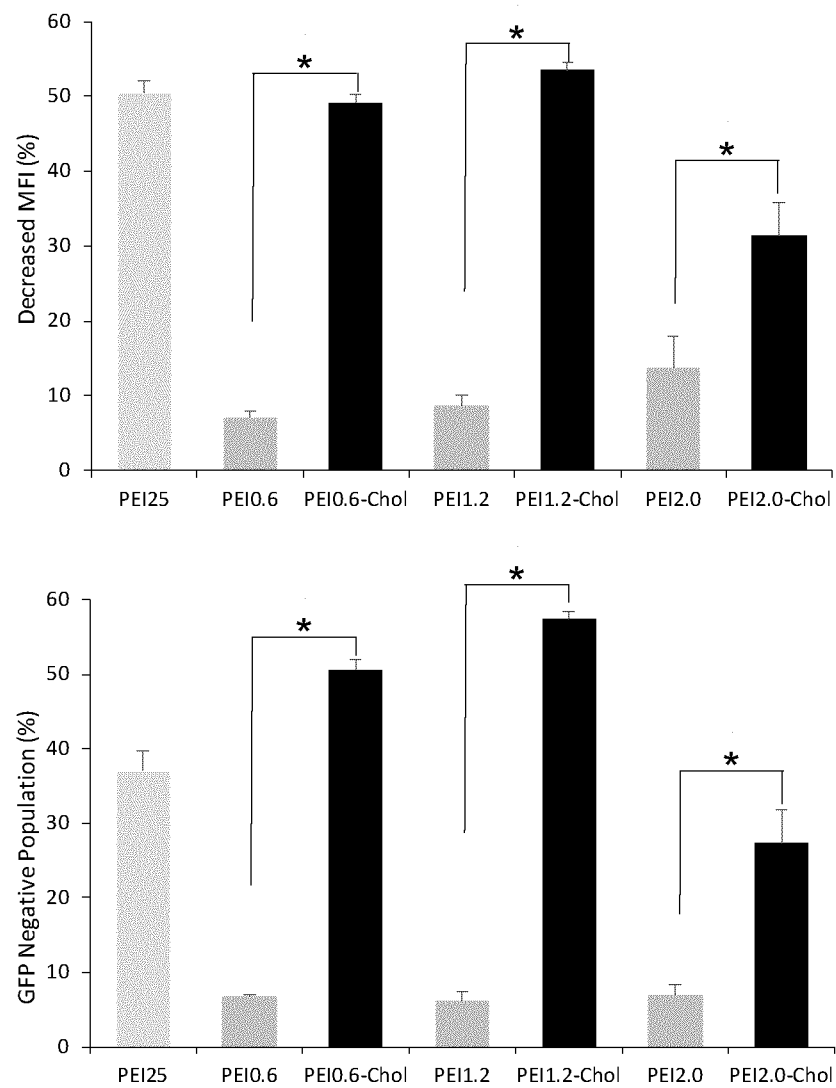
FIG. 6A are graphs showing GFP silencing efficiency in K562-GFP cells of Chol-substituted PEIs compared to PEI25 and corresponding parent polymers (0.6, 1.2 and 2.0 kDa PEI) on day 3, as determined by flow cytometry analysis summarized as decreased mean GFP fluorescence per cell (top graph) and as percentage of GFP-silenced cell population (bottom graph).
Figure 6B:
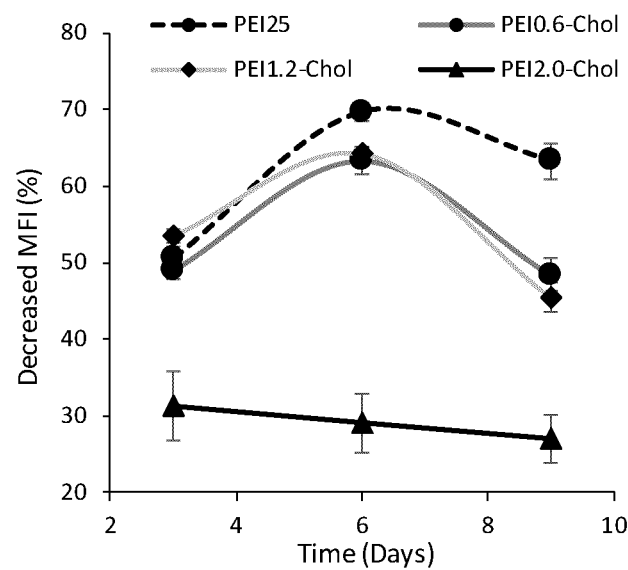
FIG. 6B are graphs showing GFP silencing efficiency of Chol-substituted PEIs compared to PEI25 at different time points, as determined by flow cytometry analysis summarized as decreased mean GFP fluorescence per cell (top graph) and as percentage of GFP-silenced cell population (bottom graph).
Figure 6B:
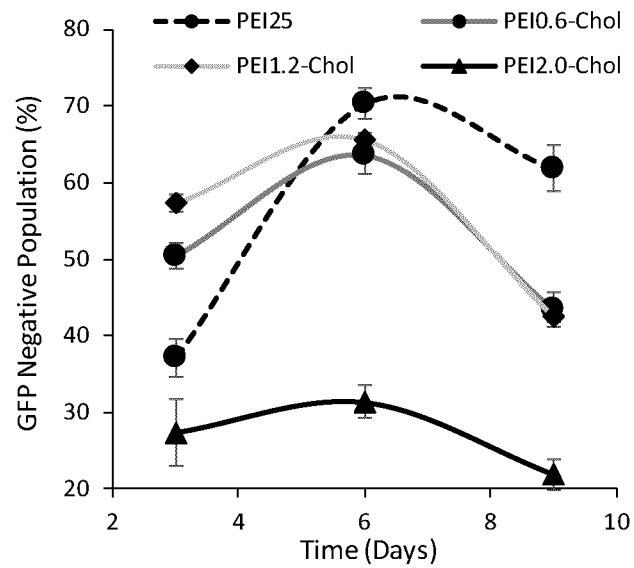

The relative efficiencies of PEI-Chol polymers for siRNA delivery were next assessed by silencing GFP expression in permanently GFP-expressing K562 (K562-GFP) cells. The silencing efficiency was assessed compared to parent polymers (day-3) and broadly acting transfecting agent (PEI25) at three time points (day 3, 6 and 9) using the complexes of ratio 12:1 (polymer:siRNA), and 60 nM siRNA. The silencing efficacy was expressed in terms of decreased mean GFP fluorescence of cell population as well as reduction in percentage of GFP-expressing cell population. In general, silencing efficacy of PEI-Chol polymers was proportional to the extent of Chol substitution; the higher the substitution, the better the silencing efficacy (FIGS. 5A-C). The efficacy of PEI-Chol was significantly higher than corresponding parent polymers and it was higher or comparable to the reference carrier, PEI25 (FIG. 6A). Maximal silencing of 60-70% was achieved based on mean fluorescence intensity, with as much as ~65% of cells experiencing GFP silencing. The beneficial effect of Chol substitution for GFP silencing was most significant ($p<0.001$) in PEI0.6 and PEI1.2 compared to higher molecular weight PEI2.0. Time-course studies indicated a sustained silencing activity, where maximum silencing was observed on day-6 and a decline on day-9 (FIG. 6A-B). The silencing efficacy of PEI-Chol polymers was compared with PEI25. The silencing efficacy of PEI0.6-Chol and PEI1.2-Chol was higher or comparable to PEI25 efficacy on day-3 and day-6. On day-9, the silencing efficacy of PEI0.6-Chol and PEI1.2-Chol was lower than PEI25. The efficacy of PEI2.0-Chol was significantly lower, again confirming the beneficial effect of lower MW PEIs as the backbone for Chol substitution.

Inhibition of K562 Cell Growth with BCR-Abl Silencing

Figure 7A:
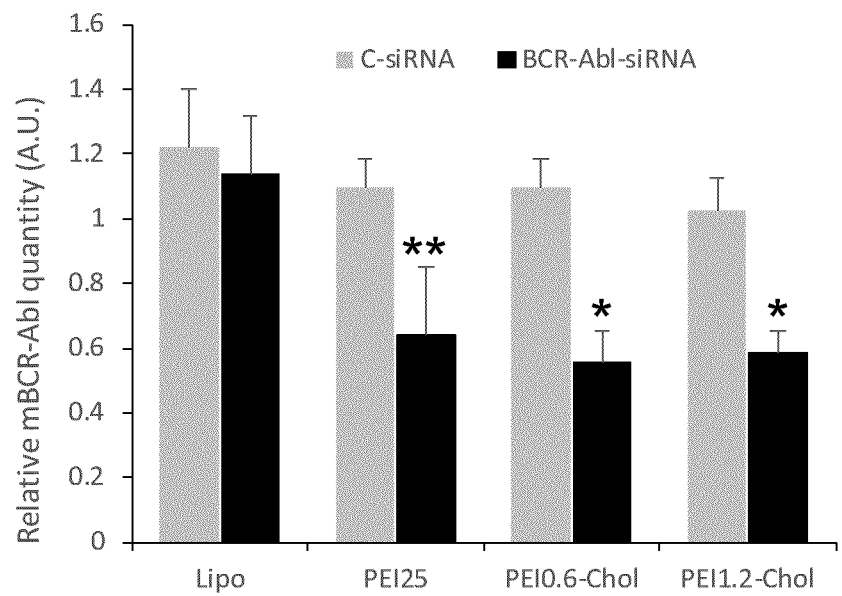
FIG. 7A is a graph showing changes in BCR-Abl mRNA levels in wild-type K562 cells (K562-wt) as quantified through RT-PCR (*p<0.01, **p<0.05).
Figure 7B:
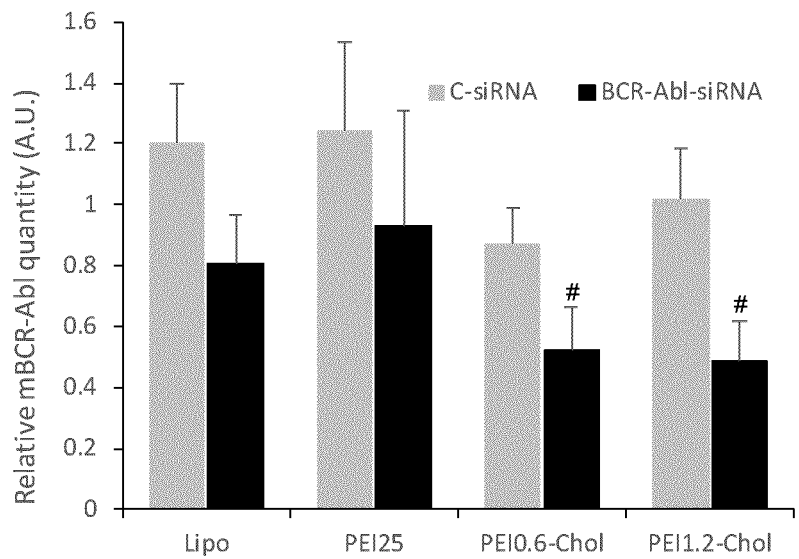
FIG. 7B is a graph showing changes in BCR-Abl mRNA levels in K562-GFP cells as quantified through RT-PCR (*p<0.01, **p<0.05).

The possibility of silencing the endogenous gene BCR-Abl and its consequence on the growth of CML cells was investigated. The changes in BCR-Abl mRNA levels in K562 and K562-GFP cells were determined using best performing PEI-Chols in GFP silencing. Control (scrambled) siRNA (C-siRNA) was included to determine non-specific effect of complex exposure and carriers Lipofectamine™ 2000 and PEI25 were used as reference carriers (FIGS. 7A-B). The siRNA delivery by Lipofectamine™ 2000 did not significantly affect the BCR-Abl mRNA levels in both cells 3 days after treatment. The siRNA delivery by PEI25 led to reduction of BCR-Abl mRNA levels, but the outcome was marginal. siRNA delivery by PEI0.6-Chol and PEI1.2-Chol showed significant (p<0.01) reduction of BCR-Abl mRNA levels, which was ~40% in both cell lines. The silencing was consistently sustained until day-6 (not shown). C-siRNA did not give any significant change in BCR-Abl levels.

Figure 8A:
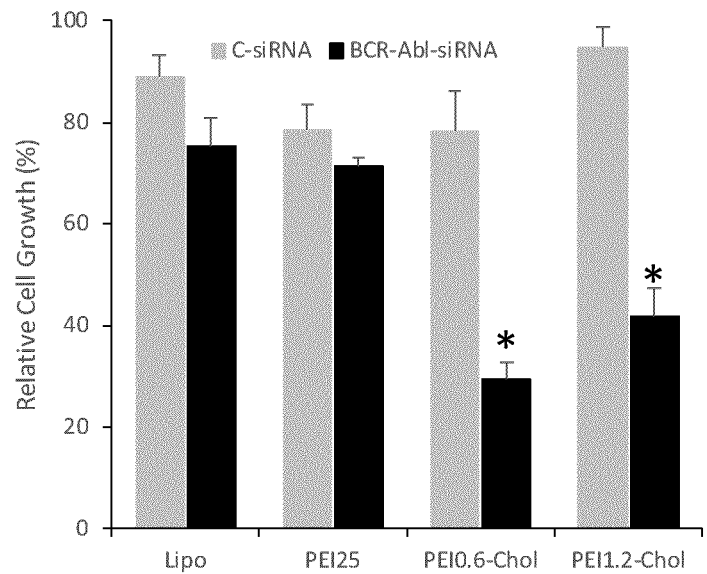
FIGS. 8A-D are graphs showing growth inhibition of CML cells (K562-wt) analyzed through MTT assay after the treatment with PEI-Chol/siRNA complexes compared with Lipofectamine™2000 and PEI25 as the function of BCR-Abl siRNA (FIG. 8A), KSP siRNA (FIG. 8B), polymer/siRNA ratio (w/w) in complexes compositions (FIG. 8C) and post transfection time (FIG. 8D). The analysis is summarized as the relative cell viability compared to the cells without any treatment (latter taken as 100%), *p<0.01, **p<0.001.

The effect of BCR-Abl siRNA delivery on cell growth in K562-wt cells was evaluated using complexes of three different polymer:siRNA ratio (6, 9 and 12, w/w) and at day 3, 6 and 9. The results showed that each variable (polymer type, siRNA concentration and polymer:siRNA ratio) showed an impact in growth inhibition due to BCR-Abl silencing (FIGS. 8A-D). At 60 nM, PEI-Chol/BCR-Abl siRNA complexes (polymer:siRNA ratio of 12) exhibited strong growth inhibition (60 to 70%) in K562-wt cells while the performances of reference carriers Lipofectamine™ 2000 and PEI25 were insignificant (FIG. 8A). PEI0.6-Chol and PEI1.2-Chol displayed significant performance, further confirming that Chol grafting onto smaller polymeric backbones were again more beneficial for siRNA delivery. Time-course studies showed a strong performance with PEI-Chol polymer to achieve a sustained growth inhibition of CML cells compared to both commercial transfecting agents (FIG. 8D); the effect was observed until day 9 (>50% cell death), indicating an extended impact of the specific siRNA delivery. The performance of PEI0.6-Chol appeared to be superior to PEI1.2-Chol indicating the better impact of smaller polymeric backbone in BCR-Abl-siRNA delivery. The impact of polymer: siRNA composition (ratio) in growth inhibition of CML cells after BCR-Abl-siRNA delivery (FIG. 8C) was also explored. The results indicate that a higher polymer:siRNA composition yielded a better effect.

Figure 8B:
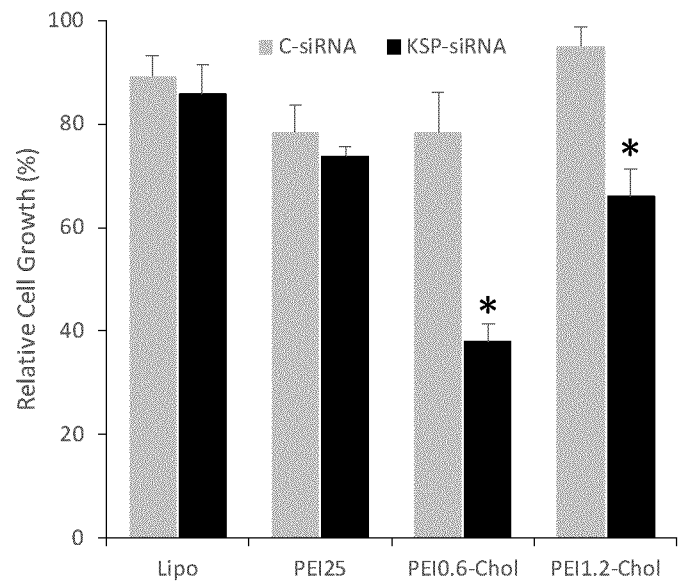
Figure 8C:
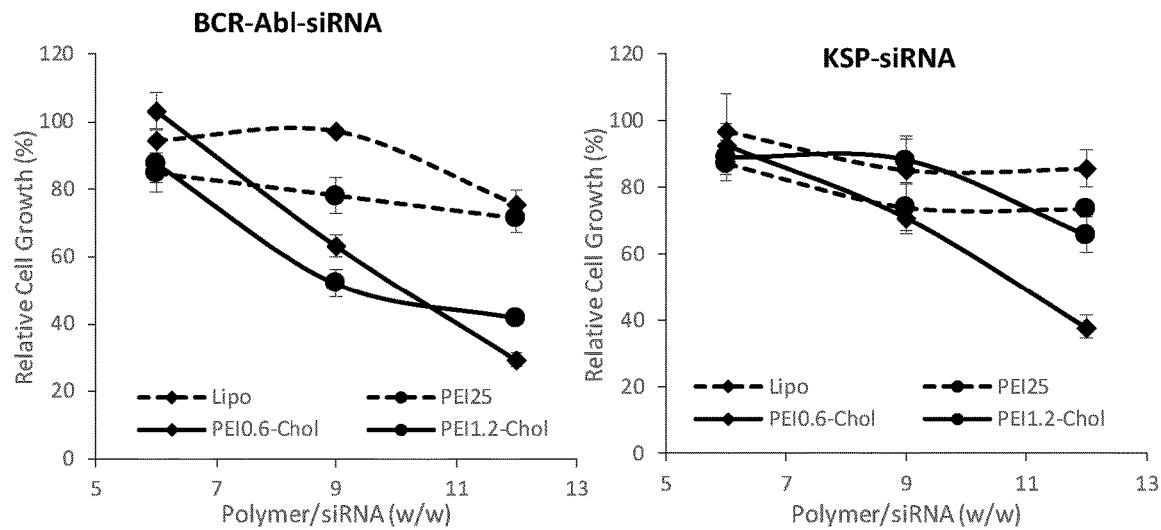
Figure 8D:
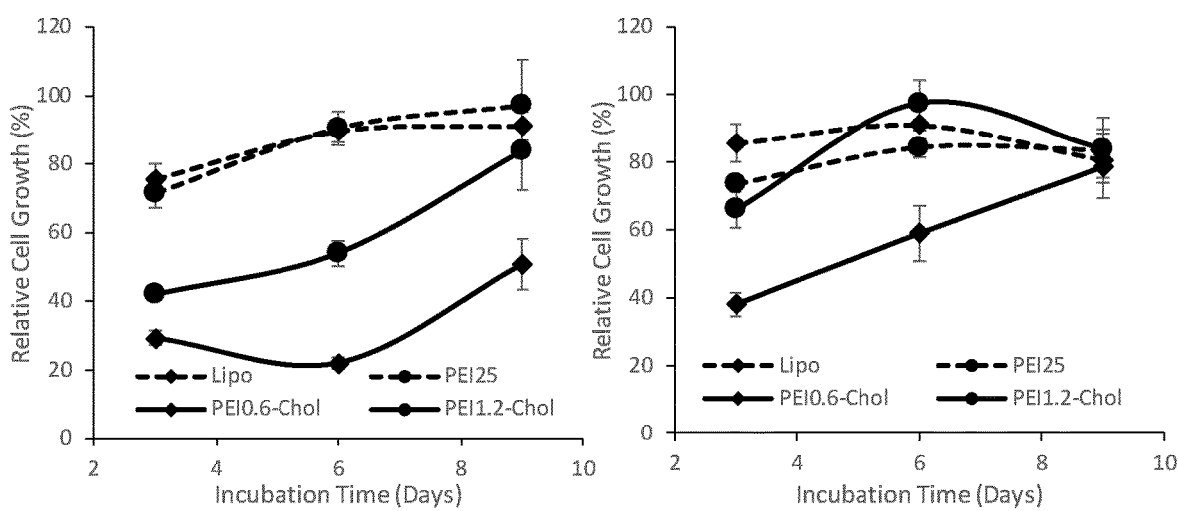

The siRNA delivery efficiency of PEI-Chol polymers was validated by performing an additional anti-proliferative study using KSP as a second therapeutic target. Like BCR-Abl inhibition, the impact of KSP siRNA delivery was significantly higher (30 to 40%) with PEI-Chol polymers (FIG. 8B). The siRNA delivery with Lipofectamine™ 2000 and PEI25 was not effective like BCR-Abl delivery. The time course-study indicated PEI0.6-Chol to be the best carrier to inhibit cell growth as compared to PEI1.2-Chol, Lipofectamine™ 2000 and PEI25 (FIG. 8D). With complexes formulated at different polymer:siRNA compositions using KSP siRNA, the performance of PEI0.6-Chol was again significantly better at higher ratios as compared to other carriers (FIG. 8C).

Figure 9A:
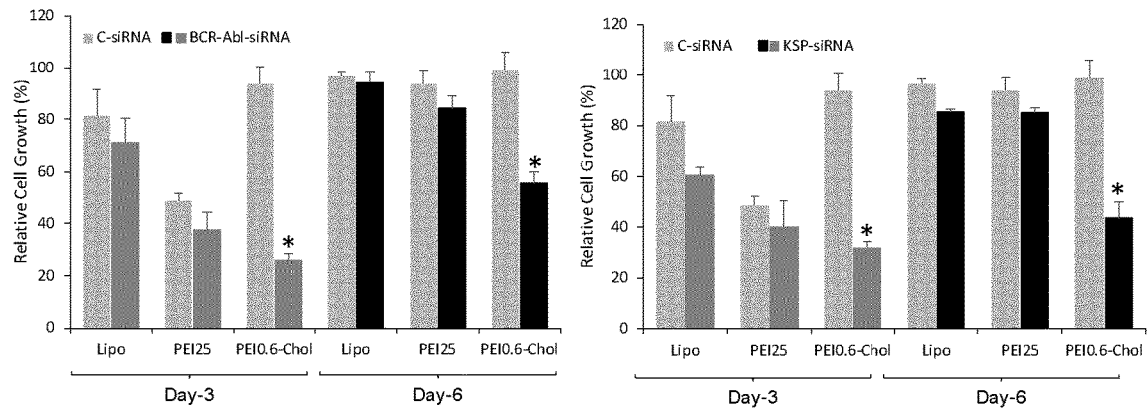
FIGS. 9A-B are graphs showing inhibition of growth in K562-GFP cells (FIG. 9A) and MDA-231 cells (FIG. 9B) analyzed through the MTT assay after treatment with polymer/siRNA complexes for day-3 and day-6. The analysis is summarized as the relative cell viability compared to the cells without any treatment (latter taken as 100%), *p<0.01.
Figure 9B:
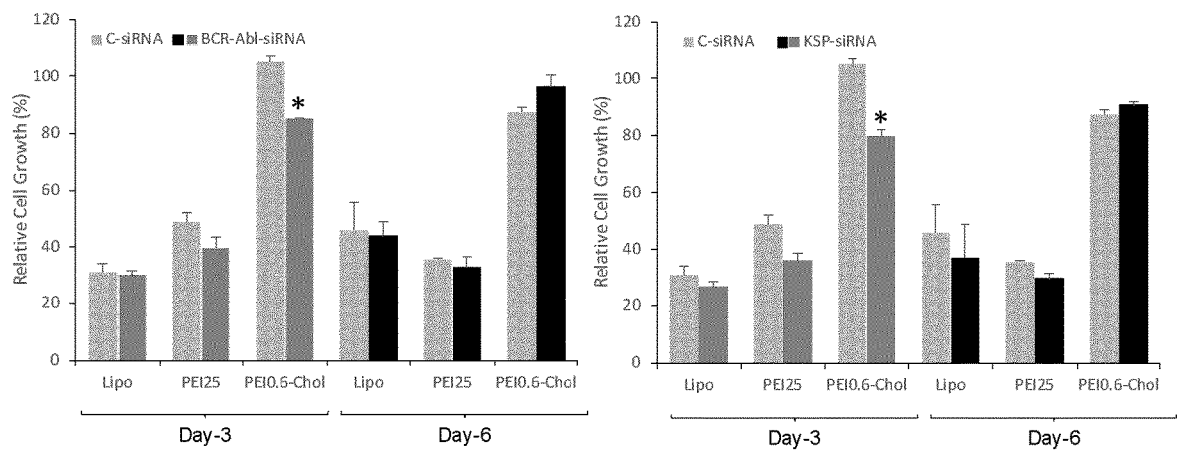

An additional study was performed to explore the impact of BCR-Abl and KSP siRNA delivery in cell growth inhibition of K562-GFP and attachment-dependent MDA-231 cells (FIGS. 9A-B). The most effective PEI0.6-Chol at optimal composition (polymer:siRNA ratio of 12 and at 60 nM siRNA concentration) was used. As in K562-wt cells, the delivery of BCR-Abl and KSP siRNA with PEI0.6-Chol significantly inhibited the growth of K562-GFP cells while the effect was negligible with Lipofectamine™ 2000 and PEI25. The effect of siRNA delivery in these particular cells was observed until day-6. However, in breast cancer cells, the efficiency of both siRNAs (BCR-Abl and KSP) was minimal and as usual the impact of PEI25 and Lipofectamine™2000 was negligible as they showed severe cellular toxicity (as indicated by low relative growth in FIGS. 9A-B).

Figure 10:
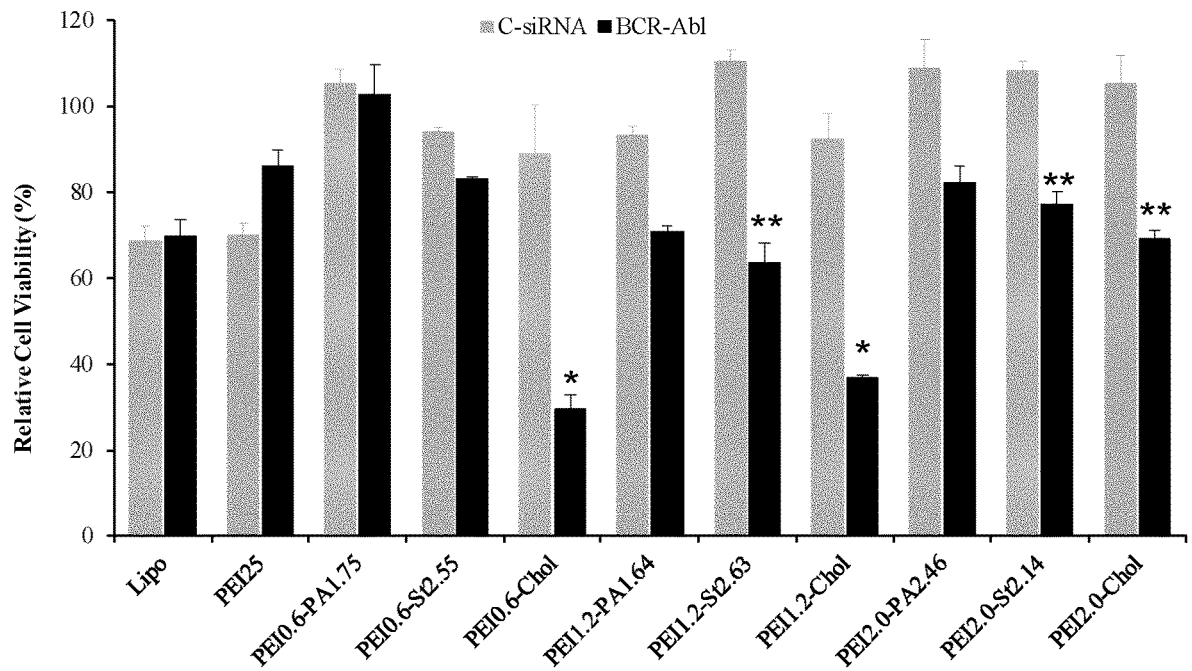
FIG. 10 is a graph showing inhibition of growth in K562-wt cells analyzed through the MTT assay after treatment with polymer/siRNA complexes for 3 days. In addition to cholesterol substitution, polymers with palmitic acid (PA)

The efficiency of newly prepared PEI-Chol polymers was compared with aliphatic lipid-substituted PEIs for BCR-Abl delivery to K562-wt cells. PEIs (0.6, 1.2 and 2.0 kDa) grafted with aliphatic lipids palmitic acid (C16) and stearic acid (C18) were prepared for this purpose (Table 1), and BCR-Abl siRNA polyplexes were formulated. The impact of siRNA delivery with aliphatic lipid-grafted PEIs on cell growth inhibition was observed on day-3 (FIG. 10), with PEI-Chol polymers showing more prominent effects on the cells. The aliphatic lipid-grafted PEI0.6 was ineffective. With PEI1.2, some promising results were obtained with palmitic and stearic acid derivatives, but the resultant cell growth inhibition was not as effective as cholesterol derivatives. Interestingly with PEI2.0, some growth inhibition was obtained with both aliphatic lipid and Chol-substituted polymer.

To explore the effect of siRNA on clonal expansion capacity of progenitor cells, the colony formation efficacy of K562-wt cells after BCR-Abl delivery was monitored. These cells formed distinct relatively flattened, spread colonies at week 1 that became more expanded on week 2. The difference in colony formation was clearly observed as the function of BCR-Abl silencing. At both time points, cells treated with BCR-Abl complexes with reference carriers, Lipofectamine™ 2000 and PEI25 showed negligible effect in colony numbers while the cells treated with PEI-Chol/BCR-Abl siRNA complexes showed significant decline in colonies (FIGS. 11A-B).

Cell Apoptosis after BCR-Abl Treatment

Figure 12A:
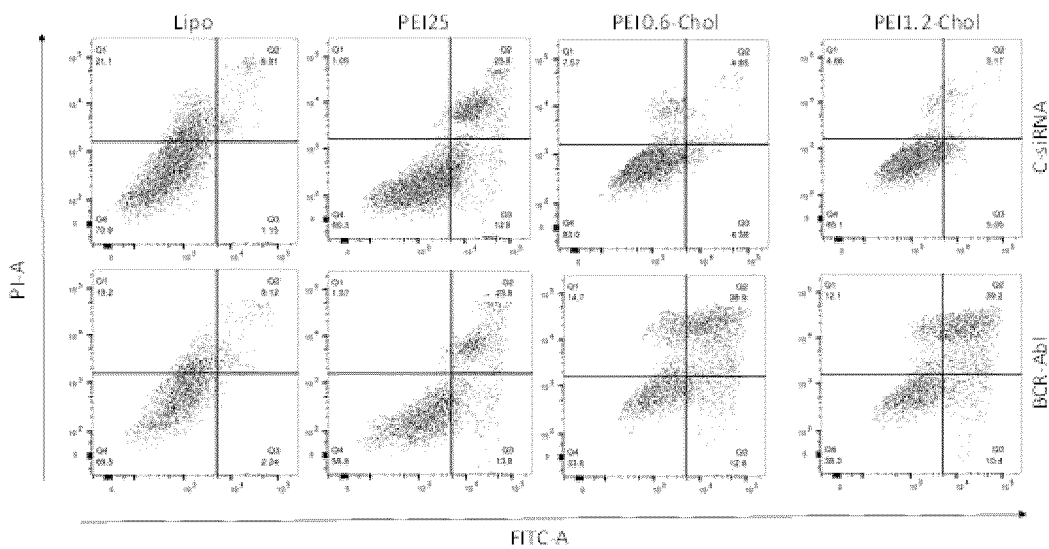
Figure 12B:
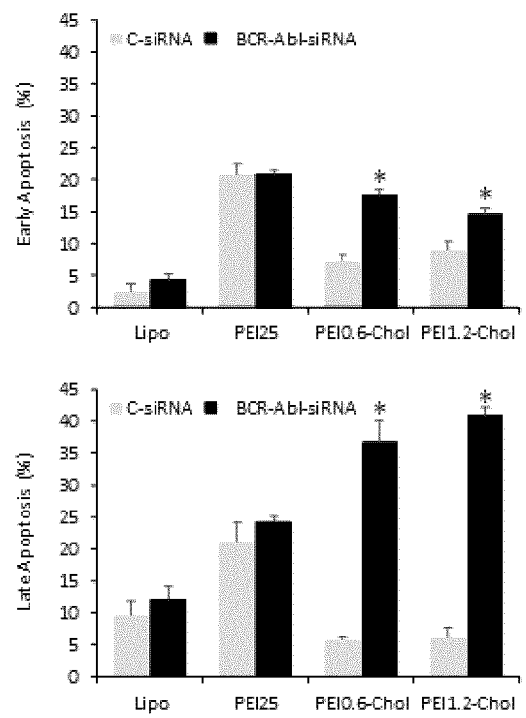
Figure 12C:
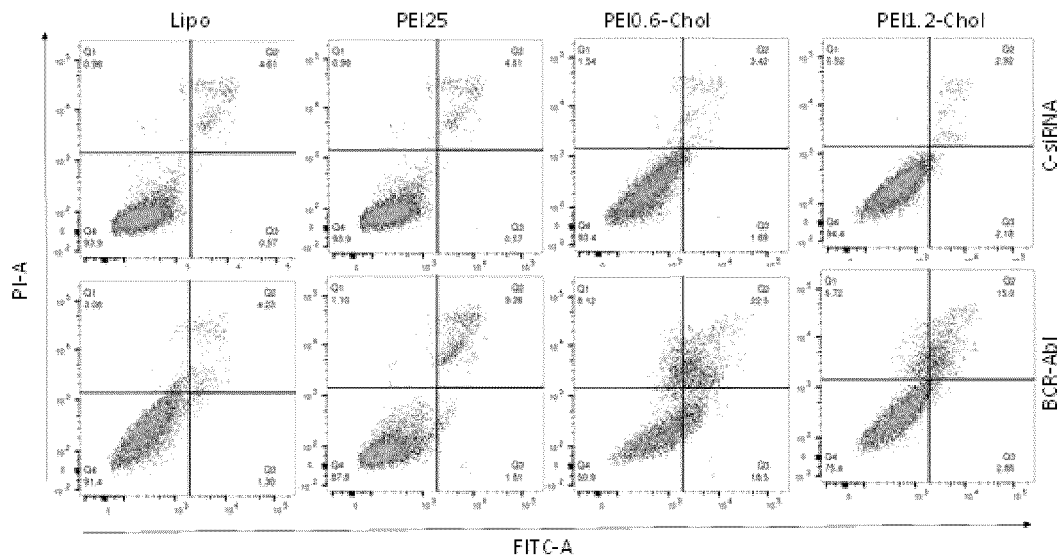
Figure 12D:
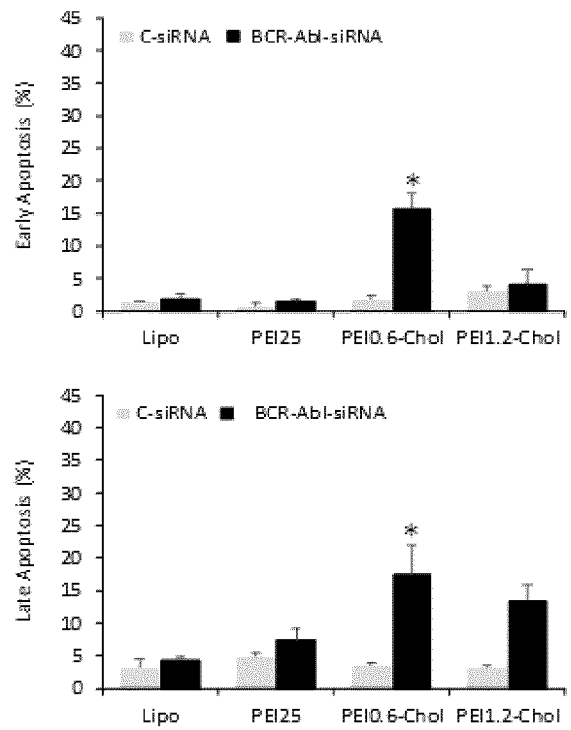

Considering the impact of BCR-Abl silencing to induce apoptosis (38), the extent of apoptosis in K562-wt cells after treatment with PEI-Chol/BCR-Abl complexes (ratio 12, w/w and 60 nM siRNA) was explored. Based on PI- and Annexin V-positive populations, the reference carrier Lipofectamine™2000 and PEI25 did not induce apoptosis, consistent with the results from the MTT assay. The level of apoptosis in BCR-Abl complexes of PEI0.6-Chol and PEI1.2-Chol was significantly higher than control siRNA treatments; on day-3, both the polymers showed prominent effect in both late apoptosis (PI-positive cells) and early apoptosis (Annexin V-positive cells) markers (FIGS. 12A-B). While on day-6, the level of apoptosis was slightly declined in both carriers however PEI0.6-Chol was still more effective (FIGS. 12C-D). It appears that successfully depleting the oncogenic target BCR-Abl resulted in a substantial increase in apoptosis.

GFP Silencing with Histidine Coupled Polymers

The PEI polymers coupled with cholesterol and histidine were investigated in K562-GFP cells to determine if the GFP expression can be silenced. As can be seen in FIG. 13, the polymers coupled with histidine in addition to cholesterol were effective in reducing the GFP fluorescence after 3 days of treatment, indicating the effectiveness of these polymers for siRNA mediated gene silencing in CML cells. Delivering a control siRNA did not change GFP expression, indicating a specific effect by the GFP siRNA. All levels of histidine substitution (from H0 to H3, where the feed ratio of histidine ranged from 0 to 3) were effective in siRNA delivery and GFP silencing.

Overall, the functional outcomes of the above studies revealed that Chol- and histidine-grafting on low MW PEIs is a highly promising to design effective nucleic acid delivery vehicles. The silencing of a reporter gene (GFP) in CIVIL cells was proportional to the extent of Chol-substitution; the higher the substitution, the better the silencing efficacy for particular MW polymers. Without being bound to any theory, this may be due to better cellular uptake since hydrophobic modification of low MW PEIs generally improves cellular uptake of complexes (1, 6). If the efficacy of PEI-Chols among different polymer backbones is compared, higher efficacy was obtained with lower MW backbones, which indicated that a proper balance in lipophilicity vs. cationic backbone was a crucial factor (35). A significant silencing of endogenous BCR-Abl gene was observed where the efficacy was higher in lower MW PEIs (0.6 and 1.2 kDa). The inhibition of cell growth was more promising than previous findings obtained by using saturated aliphatic lipid grafted PEI carriers (36). This observation was also unlike previous studies on siRNA delivery with several types of breast cancer cells (3) and acute myeloid leukemia cells (18), where high MW PEIs displayed improved efficiency after hydrophobic (aliphatic lipid) modification. It was previously appreciated that high MW PEIs are better in gene delivery efficiency (12, 13), but this observation seems to be reversed in the case of Chol-grafted low MW PEIs acting on CIVIL cells. The uptake route of hydrophobically-modified PEIs was determined to be predominantly through clathrin-mediated endocytosis (CME), whereas the parent polymers followed caveoline-mediated endocytosis (CvME) as well as micropinocytosis (16). The differences in uptake efficiency among Chol derivatives from different backbones (0.6, 1.2 and 2.0 kDa) may be due to differences in uptake route generated after chemical modification.

The impact of BCR-Abl mRNA silencing was reflected in the growth inhibition of CML cells. The outcome was varied based different factors such as complex composition (polymer/siRNA ratios), incubation time and siRNA concentration. In growth inhibition studies, the effectiveness of PEI0.6-Chol and PEI1.2-Chol among the PEI-Chols was quite impressive (where >70% inhibition of cell growth was observed), unlike Chol-substituted PEI2.0. The impact of BCR-Abl siRNA delivery was further observed in the colony formation potentiality of K562-wt cells. Since colony formation is an indication of progenitor cells to display self-renewal, siRNA delivery with select polymers effectively diminished the self-renewal capability of progenitor cells among the K562 population. The levels of cellular apoptosis after treatment with BCR-Abl complexes also confirmed the superior efficacy of PEI0.6-Chol and PEI1.2-Chol polymer. On the other hand, PEI2.0-Chol was not effective in inhibiting cell growth, even though cell uptake and GFP silencing was promising with this polymer. Presumably stronger siRNA binding by this polymer did not release sufficient siRNA into cytoplasm for a significant silencing effect on cell viability. The findings from the Annexin V assay confirm the apoptosis of CML cells after specific siRNA treatment. To further validate the versatility of PEI-Chol polymers for siRNA delivery, an additional anti-proliferative experiment was performed using KSP as a second target in CML cells. The KSP is member of kinesin superfamily of microtubule-based motors, kinesin Eg5, and is involved in centrosome separation, bipolar assembly and maintenance during mitosis (32). Being over-expressed in cancerous cells including CML cells, KSP could also be a viable target in siRNA therapy since its inhibition can block the formation bipolar mitotic spindles causing cell-cycle arrest and eventually induce cell apoptosis (27). The impact of KSP-siRNA delivery was significant and it was as prominent as BCR-Abl siRNA delivery in K562 cells. The additional efficacy observed with KSP siRNA further proves the suitability of PEI-Chol polymers in delivering different siRNAs for an effective CML therapy and opens the possibility for combinational (i.e., multiple siRNAs) therapy. It must be noted that two broadly acting commercial transfection reagents Lipofectamine™ 2000 and PEI25 were ineffective in inhibiting growth of K562 cells with the delivery of BCR-Abl and KSP siRNAs, as can be seen in FIGS. 8A-D and FIGS. 9A-B. This clearly demonstrated the utility of the PEI-Chol polymers for effectively delivering polynucleotides to influence the fate of the attachment-independent cells. As a further investigation of the versatility of PEI-Chol polymers, siRNA delivery was investigated in attachment-dependent breast cancer MDA-231 cells, but the polymers unexpectedly turned out to be relatively ineffective in these cells. Different siRNAs have been delivered to breast cancer cells using aliphatic lipid-grafted PEIs (3), but these polymers were typically derived from PEI2 and not smaller PEIs. The inefficacy of these polymers in breast cancer cells indicates the specificity of the highly hydrophobic PEI-Chol polymers in attachment-independent cells. It is possible that the internalization pathway between the two classes of cells were distinctly different, so that different carriers were optimal for siRNA in each type of cells. PEI-Chol polymers in this regard seem to be optimal for anchorage-independent cells. Different factors (e.g., the nature of carriers, cell phenotype, type of target gene) were observed to crucially affect the efficacy of the reported non-viral carriers (28). While the selected commercial carriers appeared to enhance cell delivery of siRNA and silence reporter genes, only particular types of Chol-grafted PEIs were found consistently effective in the CML cells. Unlike the general expectation, Chol-grafting was most beneficial only in LMW PEIs (0.6 and 1.2 kDa) as compared to higher MW PEIs (2.0 kDa) in designing nano-carriers for siRNA delivery to CML cells.

It should be apparent, however, to those skilled in the art that many more modifications besides those already described are possible without departing from the inventive concepts herein. The inventive subject matter, therefore, is not to be restricted except in the scope of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

1. Abbasi M, Lavasanifar A, Berthiaume L G, Weinfeld M, Uludag H. Cationic polymer-mediated small interfering RNA delivery for P-glycoprotein down-regulation in tumor cells. Cancer. 2010; 116:5544-54.
2. Aigner A, Fischer D, Merdan T, Brus C, Kissel T, Czubayko F. Delivery of unmodified bioactive ribozymes by an RNA-stabilizing polyethylenimine (LMW-PEI) efficiently down-regulates gene expression. Gene therapy. 2002; 9:1700-7.
3. Aliabadi H M, Mandipoor P, Uludag H. Polymeric delivery of siRNA for dual silencing of Mcl-1 and P-glycoprotein and apoptosis induction in drug-resistant breast cancer cells. Cancer gene therapy. 2013; 20:169-77.
4. Assmann G, Nofer J R. Atheroprotective effects of high-density lipoproteins. Annual review of medicine. 2003; 54:321-41.
5. Baccarani M, Cortes J, Pane F, Niederwieser D, Saglio G, Apperley J, et al. Chronic myeloid leukemia: an update of concepts and management recommendations of European LeukemiaNet. Journal of clinical oncology: official journal of the American Society of Clinical Oncology. 2009; 27:6041-51.
6. Bahadur K C, Landry B, Aliabadi H M, Lavasanifar A, Uludag H. Lipid substitution on low molecular weight (0.6-2.0 kDa) polyethylenimine leads to a higher zeta potential of plasmid DNA and enhances transgene expression. Acta biomaterialia. 2011; 7:2209-17.
7. Bajaj A, Kondaiah P, Bhattacharya S. Synthesis and gene transfection efficacies of PEI-cholesterol-based lipopolymers. Bioconjugate chemistry. 2008; 19:1640-51.
8. Bolcato-Bellemin A L, Bonnet M E, Creusat G, Erbacher P, Behr J P. Sticky overhangs enhance siRNA-mediated gene silencing. Proceedings of the National Academy of Sciences of the United States of America. 2007; 104:16050-5.
9. Chabaud P, Camplo M, Payet D, Serin G, Moreau L, Barthelemy P, et al. Cationic nucleoside lipids for gene delivery. Bioconjugate chemistry. 2006; 17:466-72.
10. Duxbury M S, Ashley S W, Whang E E. RNA interference: a mammalian SID-1 homologue enhances siRNA uptake and gene silencing efficacy in human cells. Biochemical and biophysical research communications. 2005; 331:459-63.
11. Furgeson D Y, Kim S W. Linear polyethylenimine-sterol conjugates for gene delivery. U.S. Pat. No. 7,183,263, issued Feb. 27, 2007.
12. Godbey W T, Wu K K, Mikos A G. Tracking the intracellular path of poly(ethylenimine)/DNA complexes for gene delivery. Proceedings of the National Academy of Sciences of the United States of America. 1999; 96:5177-81.
13. Godbey W T, Wu K K, Mikos A G. Size matters: molecular weight affects the efficiency of poly(ethylenimine) as a gene delivery vehicle. Journal of biomedical materials research. 1999; 45:268-75.
14. Goldman J M, Melo J V. Chronic myeloid leukemia—advances in biology and new approaches to treatment. The New England journal of medicine. 2003; 349:1451-64.
15. Grzelczak M, Vermant J, Furst E M, Liz-Marzan L M. Directed self-assembly of nanoparticles. ACS nano. 2010; 4:3591-605.
16. Hsu C Y, Uludag H. Cellular uptake pathways of lipid-modified cationic polymers in gene delivery to primary cells. Biomaterials. 2012; 33:7834-48.
17. Kim W J, Chang C W, Lee M, Kim S W. Efficient siRNA delivery using water soluble lipopolymer for anti-angiogenic gene therapy. Journal of controlled release: official journal of the Controlled Release Society. 2007; 118:357-63.
18. Landry B, Aliabadi H M, Samuel A, Gul-Uludag H, Jiang X, Kutsch O, et al. Effective non-viral delivery of siRNA to acute myeloid leukemia cells with lipid-substituted polyethylenimines. PloS one. 2012; 7:e44197.
19. Landry B, Valencia-Sema J, Gul-Uludag H, Jiang X, Janowska-Wieczorek A, Brandwein J, et al. Progress in RNAi-mediated Molecular Therapy of Acute and Chronic Myeloid Leukemia. Molecular therapy Nucleic acids. 2015; 4:e240.
20. Larsen H O, Roug A S, Nielsen K, Sondergaard C S, Hokland P. Nonviral transfection of leukemic primary cells and cells lines by siRNA-a direct comparison between Nucleofection and Accell delivery. Experimental hematology. 2011; 39:1081-9.
21. Ley T J et al. (Cancer Genome Atlas Research Network). Genomic and epigenomic landscapes of adult de novo acute myeloid leukemia. N Engl J Med. 2013; 368:2059-74.
22. Linder M E, Deschenes R J. New insights into the mechanisms of protein palmitoylation. Biochemistry. 2003; 42:4311-20.
23. Lungwitz U, Breunig M, Blunk T, Gopferich A. Polyethylenimine-based non-viral gene delivery systems. European journal of pharmaceutics and biopharmaceutics: official journal of Arbeitsgemeinschaft fur Pharmazeutische Verfahrenstechnik eV. 2005; 60:247-66.
24. Mahato R I, Lee M, Han S, Maheshwari A, Kim S W. Intratumoral delivery of p2CMVmIL-12 using water-soluble lipopolymers. Molecular therapy: the Journal of the American Society of Gene Therapy. 2001; 4:130-8.
25. Mahato R I, Han S, Furgeson D Y. Cationic lipopolymer as biocompatible gene delivery agent. U.S. Pat. No. 6,696,038, issued Feb. 24, 2004.
26. Mahato R I, Han S, Furgeson D Y, Anwer K. Novel cationic lipopolymer as a biocompatible gene delivery agent. US Patent Application Publication No. 2004/0142474, published Jul. 22, 2004.
27. Marra E, Palombo F, Ciliberto G, Aurisicchio L. Kinesin spindle protein SiRNA slows tumor progression. Journal of cellular physiology. 2013; 228:58-64.
28. McNamara J O, 2nd, Andrechek E R, Wang Y, Viles K D, Rempel R E, Gilboa E, et al. Cell type-specific delivery of siRNAs with aptamer-siRNA chimeras. Nature biotechnology. 2006; 24:1005-15.
29. Mintzer M A, Simanek E E. Nonviral vectors for gene delivery. Chemical reviews. 2009; 109:259-302.
30. Remant Bahadur K C CKaHU. Additive nanocomplexes of cationic lipopolymers for improved non-viral gene delivery to mesenchymal stem cells. J Mater Chem B. 2015; 3:10.
31. Ren R. Mechanisms of BCR-ABL in the pathogenesis of chronic myelogenous leukaemia. Nature reviews Cancer. 2005; 5:172-83.
32. Sarli V, Giannis A. Targeting the kinesin spindle protein: basic principles and clinical implications. Clinical cancer research: an official journal of the American Association for Cancer Research. 2008; 14:7583-7.
33. Schiffer C A. BCR-ABL tyrosine kinase inhibitors for chronic myelogenous leukemia. The New England journal of medicine. 2007; 357:258-65.
34. Soutschek J, Akinc A, Bramlage B, Charisse K, Constien R, Donoghue M, et al. Therapeutic silencing of an endogenous gene by systemic administration of modified siRNAs. Nature. 2004; 432:173-8.
35. Teo P Y, Yang C, Hedrick J L, Engler A C, Coady D J, Ghaem-Maghami S, et al. Hydrophobic modification of low molecular weight polyethylenimine for improved gene transfection. Biomaterials. 2013; 34:7971-9.
36. Valencia-Sema J, Gul-Uludag H, Mandipoor P, Jiang X, Uludag H. Investigating siRNA delivery to chronic myeloid leukemia K562 cells with lipophilic polymers for therapeutic BCR-ABL down-regulation. Journal of Controlled Release. 2013; 172:495-503.
37. Wang D A, Narang A S, Kotb M, Gaber A O, Miller D D, Kim S W, et al. Novel branched poly(ethylenimine)-cholesterol water-soluble lipopolymers for gene delivery. Biomacromolecules. 2002; 3:1197-207.
38. Zhou L L, Zhao Y, Ringrose A, DeGeer D, Kennah E, Lin A E, et al. AHI-1 interacts with BCR-ABL and modulates BCR-ABL transforming activity and imatinib response of CML stem/progenitor cells. J Exp Med. 2008; 205:2657-71.

What is claimed is:

1. A compound comprising a polymer and a lipid covalently linked via N-acylation, the polymer is polyethylenimine having a molecular weight ranging from 0.6 kDa to 2.0 kDa, and the lipid is cholesterol or a derivative thereof, or lauric acid.

2. The compound of claim 1, wherein the polymer is polyethylenimine in a branched or linear form.

3. The compound of claim 1, wherein the derivative of cholesterol is cholic acid or deoxycholic acid.

4. The compound of claim 2, wherein the polymer is polyethylenimine in a branched or linear form and is coupled to histidine and cholesterol or a derivative thereof.

5. The compound of claim 1, having the formula:

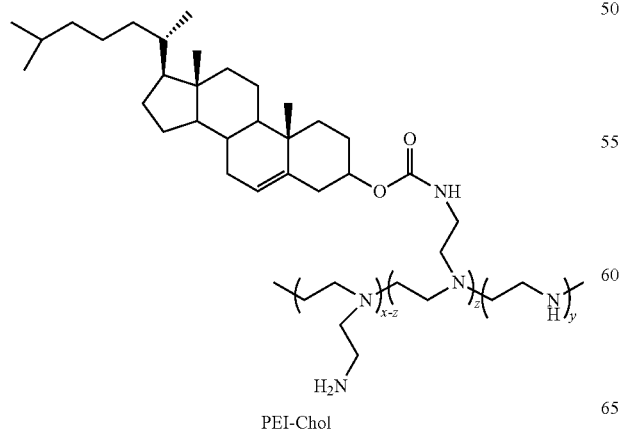

PEI-Chol wherein x, y and z are repeating units in polyethylenimine, and x is 7 to 22 repeating units, y is 14 to 44 repeating units, and z is 1 to 5 repeating units.

6. The compound of claim 1, having the formula:

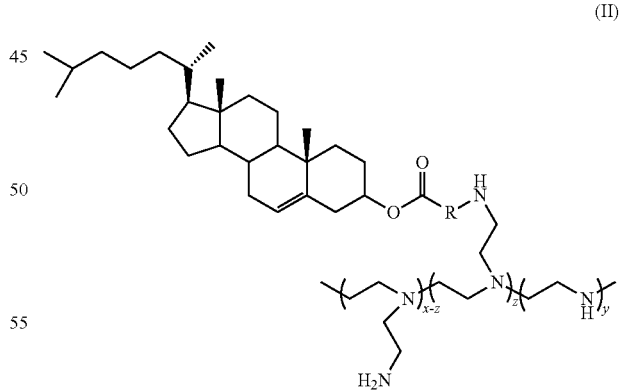

where the variable linker R is a spacer of $0<n<10$ atoms and a cleavable chemical group; and x, y and z are repeating units in polyethylenimine, and x is 7 to 22 repeating units, y is 14 to 44 repeating units, and z is 1 to 5 repeating units.

7. The compound of claim 6, wherein the chemical group is selected from disulfide, thioester, ester, orthoester, anhydride, a phosphoester, acetal, ketal, or carbonate.

8. The compound of claim 6, having the formula:

(IIa)

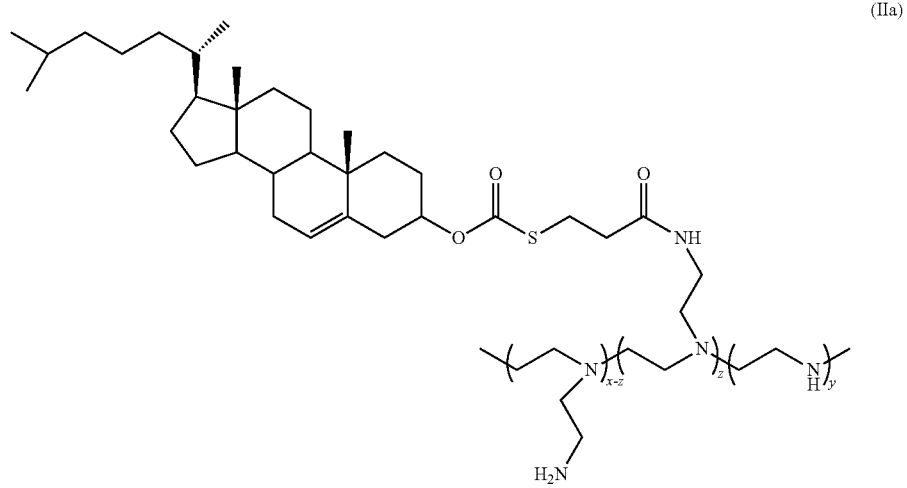

where x, y and z are repeating units in polyethylenimine, and x is 7 to 22 repeating units, y is 14 to 44 repeating units, and z is 1 to 5 repeating units.

9. The compound of claim 6, having the formula:

(IIb)

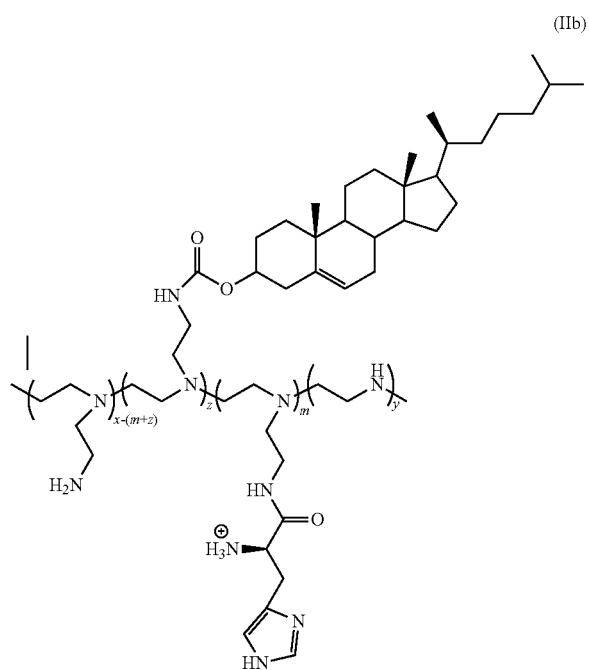

where the compound comprises a histidine group on the polymer backbone; and where x, y, z, and m are repeating units in polyethylenimine, and x is 7 to 22 repeating units, y is 14 to 44 repeating units, z is 1 to 5 repeating units, and m is 1 to 5 repeating units.

10. A nanoparticle comprising the compound of claim 1 complexed to a nucleic acid.

11. The nanoparticle of claim 10, wherein the nucleic acid is selected from siRNA, microRNA, a DNA-based oligonucleotide or antisense oligonucleotide, a peptide-nucleic acid, DNA-RNA chimeras, messenger RNA, or combinations thereof.

12. The nanoparticle of claim 11, wherein the target gene of siRNA is selected from KIF11, FLT3, STAT3, STAT5A/B, RRM2, FLT1, RUNX1, Cyclin A2, Hsp70, p65, p100/52 (NfκB ), HIF-1a, GFI-1B, Hsp27, Hsp32, CXCR4, CD44, Nucleoplasmin gene, a gene encoding an inhibitor of DNA binding protein, CD22, MAX dimerization protein 3 (MDX3) gene, or a fusion gene selected from AML1-ETO, BCR-ABL, BCR-JAK2, BCR-FGFR1, CEP110-FGFR1, ERG, EWS-FLI1, TEL-AML1, ETV6-ABL, ETV6-PDGFRB, ETV6-JAK2, ETV6-SYK2, EWS-ERG, FOP-FGFR1, HIP1-PDGFRB, H4-PDGFRB, MLL/ENL, MLLT10/AF10, MLL/AF9, a fusion gene comprising MLL, MYH11-CBFB, NUP98-NSD1, PAX3-FKHR, PML-RARA, RAB5-PDGFRB, RUNX1-RUNX1T1, TLS-FUS, or ZNF198-FGFR1.

13. A composition comprising the nanoparticle of claim 10, and a pharmaceutically acceptable carrier, a targeting ligand, an anti-fouling agent, or combination thereof.

14. The composition of claim 13, wherein the targeting ligand is selected from an antibody or fragment thereof, an aptamer from an oligonucleotide, a peptide, a protein, a polysaccharide, or a vitamin; the targeting ligand being specific for a cell surface molecule selected from JL1, CA19-9, CD2, CD3, CD5, CD19, CD20, CD33, CD34, CD38, CD44, CD52, CD74, CD96, CD99, CD117, CD135, CD166, CD184, CLL1, CXCR4, folate or folic acid, LFA-1, MMP-2, MMP-9, PTK7, sigma, transferrin, biotin, lectin, PD-1, or SMALF7.

15. The composition of claim 13, wherein the anti-fouling agent comprises a hydrophilic polymer selected from polyethylene glycol, hyaluronic acid, alginate, heparin, heparin sulfate, chondroitin sulfate, dermatan sulfate, or keratin sulfate.

16. A method of treating, preventing, or ameliorating blood cancer in a subject, comprising administering to the subject an effective amount of a compound comprising a polymer and a lipid covalently linked via N-acylation, the polymer being polyethylenimine having a molecular weight ranging from 0.6 kDa to 2.0 kDa, and the lipid being cholesterol or a derivative thereof, or lauric acid or a derivative thereof, wherein the compound is capable of delivering a ribonucleic acid; a nanoparticle comprising the compound complexed to a ribonucleic acid, or a composition comprising the compound or the nanoparticle and a pharmaceutically acceptable carrier, a targeting ligand, an anti-fouling agent, or combination thereof.

17. The method of claim 16, wherein the blood cancer is selected from chronic myeloid leukemia, acute myeloid leukemia, chronic lymphocytic leukemia, acute lymphocytic leukemia, hairy cell leukemia, meningeal leukemia, myeloma, multiple myeloma, lymphoma, non-Hodgkin lymphoma, or Hodgkin lymphoma.

18. The method of claim 16, wherein the nanoparticle comprises polyethylenimine, cholesterol or lauric acid, and siRNA, or a composition comprising same.

19. The method of claim 16, wherein the polyethylenimine has a molecular weight ranging from 0.6 kDa to 2.0 kDa.

20. The method of claim 16, further comprising administering one or more drugs selected from Alemtuzumab, Arsenic Trioxide, Asparaginase, Azacitidine, Bendamustine Hydrochloride, Belinostat, Bleomycin, Blinatumomab, Bortezomib, Bosutinib, Brentuximab, Vedotin, Busulfan, Carmustine, Carfilzomib, Cladribine, Clofarabine, Chlorambucil, Cyclophosphamide, Cytarabine, Dasatinib, Daunorubicin Hydrochloride, Dacarbazine, Daratumumab, Decitabine, Denileukin Diftitox, Doxorubicin Hydrochloride, Elotuzumab, Fludarabine Phosphate, Imatinib Mesylate, Hydroxyurea, Ibrutinib, Idarubicin Hydrochloride, Idelalisib, Intron A (Recombinant Interferon Alfa-2b), Ixazomib Citrate, Lenalidomide, Lomustine, Mercaptopurine, Mechlorethamine Hydrochloride, Methotrexate, Nelarabine, Nilotinib, Nivolumab, Obinutuzumab, Ofatumumab, Omacetaxine Mepesuccinate, Pamidronate Disodium, Panobinostat, Pegaspargase, Pembrolizumab, Plerixafor, Pomalidomide, Ponatinib Hydrochloride, Pralatrexate, Prednisone, Procarbazine Hydrochloride, Rituximab, Romidepsin, Thalidomide, Thioguanine, Tositumomab, Vincristine Sulfate, Venetoclax, Vinblastine Sulfate, Vorinostat, or Zoledronic Acid.

21. The method of claim 16, wherein the compound has the formula:

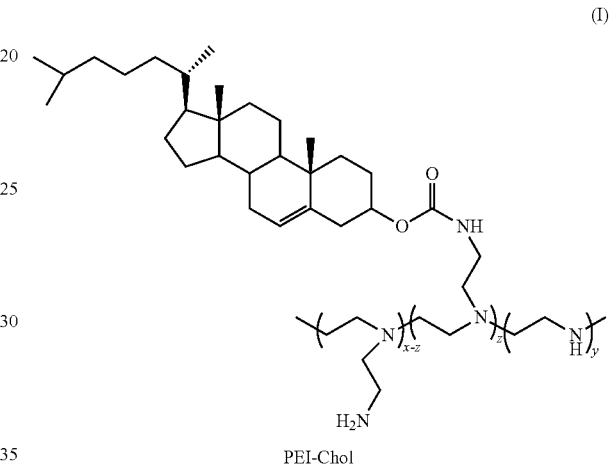

PEI-Chol wherein x, y and z are repeating units in polyethylenimine, and x is 7 to 22 repeating units, y is 14 to 44 repeating units, and z is 1 to 5 repeating units.

22. The method of claim 16, having the formula:

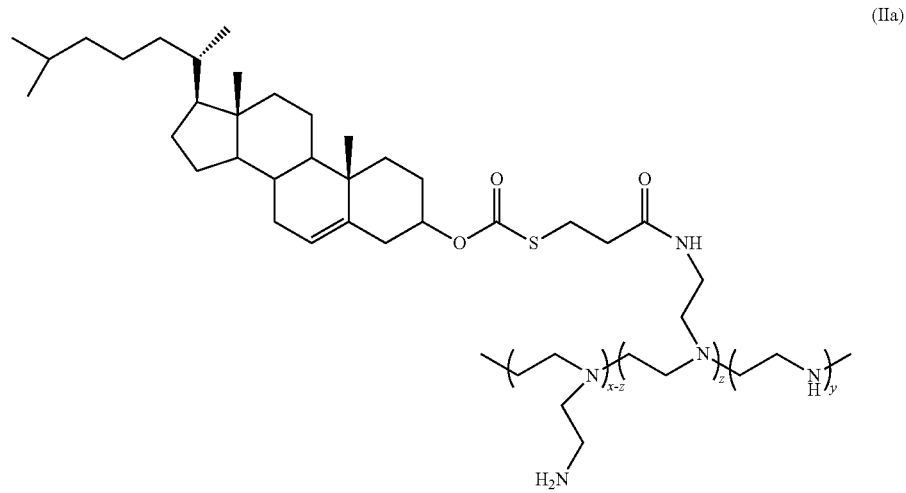

where x, y and z are repeating units in polyethylenimine, and x is 7 to 22 repeating units, y is 14 to 44 repeating units, and z is 1 to 5 repeating units.

23. The method of claim 16, having the formula:

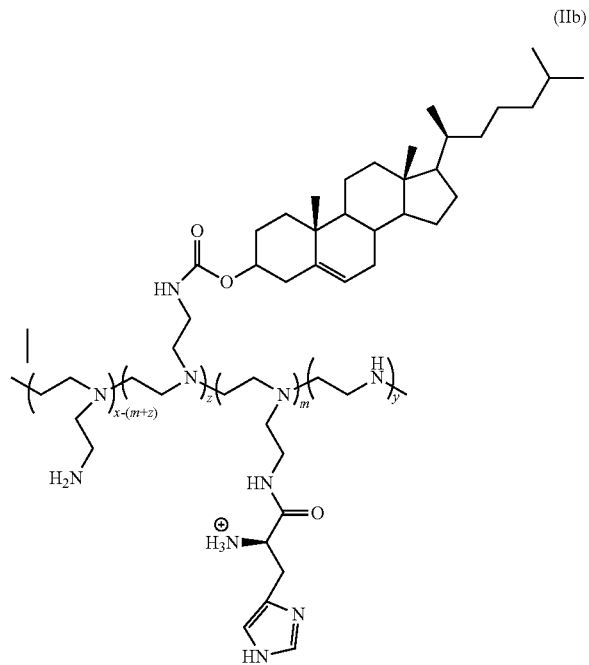

(IIb)

where the compound comprises a histidine group on the polymer backbone; and
where x, y, z, and m are repeating units in polyethylenimine, and x is 7 to 22 repeating units, y is 14 to 44 repeating units, z is 1 to 5 repeating units, and m is 1 to 5 repeating units.

24. The method of claim 16, wherein a target gene of the ribonucleic acid is selected from KIF11, FLT3, STAT3, STAT5A/B, RRM2, FLT1, RUNX1, Cyclin A2, Hsp70, p65, p100/52 (NfkB), HIF-la, GFI-1B, Hsp27, Hsp32, CXCR4, CD44, Nucleoplasmin gene, a gene encoding an inhibitor of DNA binding protein, CD22, MAX dimerization protein 3 (MDX3) gene, or a fusion gene selected from AML1-ETO, BCR-ABL, BCR-JAK2, BCR-FGFR1, CEP110-FGFR1, ERG, EWS-FLI1, TEL-AML1, ETV6-ABL, ETV6-PDG-FRB, ETV6-JAK2, ETV6-SYK2, EWS-ERG, FOP-FGFR1, HIP1-PDGFRB, H4-PDGFRB, MLL/ENL, MLLT10/AF10, MLL/AF9, a fusion gene comprising MLL, MYH11-CBFB, NUP98-NSD1, PAX3-FKHR, PML-RARA, RAB5-PDG-FRB , RUNX1-RUNX1T1, TLS-FUS, or ZNF198-FGFR1.

25. The method of claim 16, wherein the targeting ligand is selected from an antibody or fragment thereof, an aptamer from an oligonucleotide, a peptide, a protein, a polysaccharide, or a vitamin; the targeting ligand being specific for a cell surface molecule selected from JL1, CA19-9, CD2, CD3, CD5, CD19, CD20, CD33, CD34, CD38, CD44, CD52, CD74, CD96, CD99, CD117, CD135, CD166, CD184, CLL1, CXCR4, folate or folic acid, LFA-1, MMP-2, MMP-9, PTK7, sigma, transferrin, biotin, lectin, PD-1, or SMALF7.

26. The method of claim 16, wherein the anti-fouling agent comprises a hydrophilic polymer selected from polyethylene glycol, hyaluronic acid, alginate, heparin, heparin sulfate, chondroitin sulfate, dermatan sulfate, or keratin sulfate.

27. The method of claim 16, wherein the lipid is lauric acid or a derivative thereof.

28. The method of claim 16, wherein the ribonucleic acid is selected from short interfering RNA or other non-coding RNAs.

29. A method of treating, preventing, or ameliorating blood cancer in a subject, comprising administering to the subject an effective amount of a compound having the formula (I):

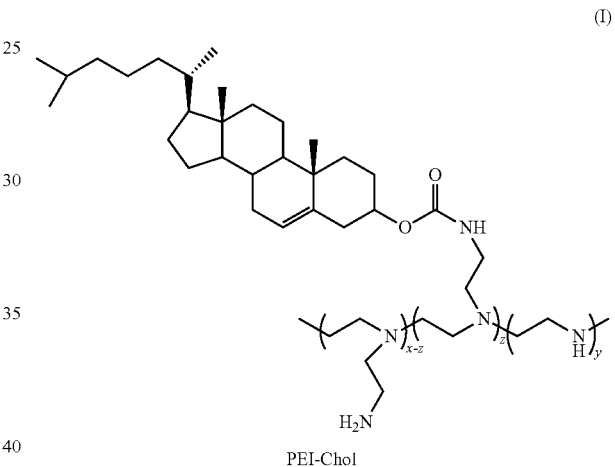

(I)

PEI-Chol wherein x, y and z are repeating units in polyethylenimine, and x is 7 to 22 repeating units, y is 14 to 44 repeating units, and z is 1 to 5 repeating units;
and wherein the compound is capable of delivering a ribonucleic acid; a nanoparticle comprising the compound complexed to a ribonucleic acid, or a composition comprising the compound or the nanoparticle and a pharmaceutically acceptable carrier, a targeting ligand, an anti-fouling agent, or combination thereof.

30. The method of claim 29, wherein the ribonucleic acid is selected from short interfering RNA or other non-coding RNAs.

* * * * *

SEQUENCE LISTING

<160> NUMBER OF SEQ ID NOS: 8

<210> SEQ ID NO 1
<211> LENGTH: 19
<212> TYPE: RNA
<213> ORGANISM: Artificial Sequence
<220> FEATURE:
<221> NAME/KEY: modified_base
<222> LOCATION: (18)..(19)
<223> OTHER INFORMATION: BCR-Abl siRNA sense strand
      u = 2'-deoxythymidine (dT)

<400> SEQUENCE: 1
gcagaguuca aaagcccuu                                              19

<210> SEQ ID NO 2
<211> LENGTH: 19
<212> TYPE: RNA
<213> ORGANISM: Artificial Sequence
<220> FEATURE:
<221> NAME/KEY: modified_base
<222> LOCATION: (1)..(2)
<223> OTHER INFORMATION: BCR-Abl siRNA antisense strand
      u = 2'-deoxythymidine (dT)

<400> SEQUENCE: 2
uucgucucaa guuuucggg                                              19

<210> SEQ ID NO 3
<211> LENGTH: 22
<212> TYPE: DNA
<213> ORGANISM: Artificial Sequence
<220> FEATURE:
<223> OTHER INFORMATION: Forward primer

<400> SEQUENCE: 3
ccaccccact tctctctaag ga                                          22

<210> SEQ ID NO 4
<211> LENGTH: 25
<212> TYPE: DNA
<213> ORGANISM: Artificial Sequence
<220> FEATURE:
<223> OTHER INFORMATION: Reverse primer

<400> SEQUENCE: 4
aatttacacg aaagcaatgc tatca                                       25

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
tcactgttct ctccctccgc                                             20

```
<210> SEQ ID NO 6
<211> LENGTH: 22
<212> TYPE: DNA
<213> ORGANISM: Artificial Sequence
<220> FEATURE:
<223> OTHER INFORMATION: Reverse primer

<400> SEQUENCE: 6
tacgaccaaa tccgttgact cc                                    22

<210> SEQ ID NO 7
<211> LENGTH: 22
<212> TYPE: DNA
<213> ORGANISM: Artificial Sequence
<220> FEATURE:
<223> OTHER INFORMATION: Forward primer

<400> SEQUENCE: 7
cattccgctg accatcaata ag                                    22

<210> SEQ ID NO 8
<211> LENGTH: 20
<212> TYPE: DNA
<213> ORGANISM: Artificial Sequence
<220> FEATURE:
<223> OTHER INFORMATION: Reverse primer

<400> SEQUENCE: 8
gatgctactg gccgctgaag                                       20
```